(12) United States Patent
Abdou

(10) Patent No.: US 8,845,701 B2
(45) Date of Patent: Sep. 30, 2014

(54) DEVICES AND METHODS FOR DYNAMIC FIXATION OF SKELETAL STRUCTURE

(71) Applicant: Samy Abdou, San Diego, CA (US)

(72) Inventor: Samy Abdou, San Diego, CA (US)

(*) Notice: Subject to any disclaimer, the term of this patent is extended or adjusted under 35 U.S.C. 154(b) by 0 days.

(21) Appl. No.: 14/146,958

(22) Filed: Jan. 3, 2014

(65) Prior Publication Data
US 2014/0180346 A1    Jun. 26, 2014

Related U.S. Application Data

(60) Division of application No. 13/846,696, filed on Mar. 18, 2013, which is a division of application No. 12/882,117, filed on Sep. 14, 2010, now Pat. No. 8,398,689, which is a continuation of application No. 11/360,038, filed on Feb. 21, 2006, now Pat. No. 7,862,588.

(60) Provisional application No. 60/749,719, filed on Dec. 12, 2005, provisional application No. 60/731,690, filed on Oct. 31, 2005, provisional application No. 60/654,602, filed on Feb. 18, 2005.

(51) Int. Cl.
| | | |
|---|---|---|
| *A61B 17/04* | (2006.01) | |
| *A61B 17/84* | (2006.01) | |
| *A61F 2/08* | (2006.01) | |
| *A61B 17/86* | (2006.01) | |

(52) U.S. Cl.
CPC ......... *A61B 17/8685* (2013.01); *A61B 17/8605* (2013.01)
USPC ...................................................... 606/300

(58) Field of Classification Search
USPC ................................. 606/260–279, 300–320
See application file for complete search history.

(56) References Cited

U.S. PATENT DOCUMENTS

| | | |
|---|---|---|
| 824,983 A | 7/1906 | Farrington |
| 944,725 A | 12/1909 | Ferguson |
| 1,015,890 A | 1/1912 | Hyde |
| 1,213,599 A | 1/1917 | Dow |
| 1,785,709 A | 4/1930 | Campau |
| 2,248,054 A | 7/1941 | Becker |
| 2,329,398 A | 9/1943 | Duffy |
| 2,370,407 A | 2/1945 | McCartney |

(Continued)

FOREIGN PATENT DOCUMENTS

| | | |
|---|---|---|
| EP | 1180348 | 2/2002 |
| FR | 2781359 | 1/2000 |

(Continued)

OTHER PUBLICATIONS

Suzuki Y., "Shape Memory and Super-Elasticity Effects in NiTi Alloys", Titanium-Zirconium, 30(4):185-192 (1982). cited by applicant.

(Continued)

*Primary Examiner* — Sameh Boles
(74) *Attorney, Agent, or Firm* — Gazdzinski & Associates, PC

(57) ABSTRACT

The disclosed screw assemblies include a screw that attaches onto the bone, a housing member that connects and interlocks the bone screw to the rod, and one or more looking members that permit immobilization of various components of the assembly relative to one another while still permitting some relative movement. The bone screws and bone screw assemblies described herein permit flexible stabilization of the spine.

24 Claims, 39 Drawing Sheets

(56) References Cited

U.S. PATENT DOCUMENTS

| | | | |
|---|---|---|---|
| 2,574,352 | A | 11/1951 | Senter |
| 3,037,596 | A | 6/1962 | Fordyce |
| 3,072,423 | A | 1/1963 | Charlton |
| 3,236,141 | A | 2/1966 | Smith |
| 3,604,487 | A | 9/1971 | Gilbert |
| 3,659,595 | A | 5/1972 | Haboush |
| 4,289,123 | A | 9/1981 | Dunn |
| 4,399,813 | A | 8/1983 | Barber |
| 4,699,076 | A | 10/1987 | Curtis |
| 4,773,402 | A | 9/1988 | Asher et al. |
| 4,877,020 | A | 10/1989 | Vich |
| 4,903,692 | A | 2/1990 | Reese |
| 4,904,110 | A | 2/1990 | Klein |
| 4,969,886 | A | 11/1990 | Cziffer et al. |
| 5,052,711 | A | 10/1991 | Pirkey et al. |
| 5,133,717 | A | 7/1992 | Chopin |
| 5,176,680 | A | 1/1993 | Vignaud et al. |
| 5,252,016 | A | 10/1993 | Schmid et al. |
| 5,275,601 | A | 1/1994 | Goglewski et al. |
| 5,336,225 | A | 8/1994 | Zang |
| 5,352,231 | A | 10/1994 | Brumfield et al. |
| 5,354,292 | A | 10/1994 | Braeuer et al. |
| 5,360,429 | A | 11/1994 | Jeanson et al. |
| 5,364,399 | A | 11/1994 | Lowery et al. |
| 5,366,455 | A | 11/1994 | Dove et al. |
| 5,423,826 | A | 6/1995 | Coates et al. |
| 5,437,672 | A | 8/1995 | Alleyne |
| 5,439,339 | A | 8/1995 | Batchelor |
| 5,474,555 | A | 12/1995 | Puno et al. |
| 5,484,440 | A | 1/1996 | Allard |
| 5,487,742 | A | 1/1996 | Cotrel |
| 5,531,747 | A | 7/1996 | Ray |
| 5,534,001 | A | 7/1996 | Schlapfer et al. |
| 5,534,027 | A | 7/1996 | Hodorek |
| 5,545,164 | A | 8/1996 | Howland |
| 5,549,612 | A | 8/1996 | Yapp et al. |
| 5,558,674 | A | 9/1996 | Heggeness et al. |
| 5,569,250 | A | 10/1996 | Sarver et al. |
| 5,578,034 | A | 11/1996 | Estes |
| 5,586,984 | A | 12/1996 | Errico et al. |
| 5,591,166 | A | 1/1997 | Bernhardt et al. |
| 5,607,426 | A | 3/1997 | Ralph et al. |
| 5,616,142 | A | 4/1997 | Yuan et al. |
| 5,649,931 | A | 7/1997 | Bryant et al. |
| 5,669,912 | A | 9/1997 | Spetzler |
| 5,672,176 | A | 9/1997 | Biedermann et al. |
| 5,676,666 | A | 10/1997 | Oxland et al. |
| 5,681,311 | A | 10/1997 | Foley et al. |
| 5,681,312 | A | 10/1997 | Yuan et al. |
| 5,681,313 | A | 10/1997 | Diez |
| 5,704,936 | A | 1/1998 | Mazel |
| 5,707,372 | A | 1/1998 | Errico et al. |
| 5,709,686 | A | 1/1998 | Talos et al. |
| 5,713,900 | A | 2/1998 | Benzel et al. |
| 5,716,357 | A | 2/1998 | Rogozinski |
| 5,733,285 | A | 3/1998 | Errico et al. |
| 5,735,853 | A | 4/1998 | Olerud |
| 5,810,819 | A | 9/1998 | Errico et al. |
| 5,876,402 | A | 3/1999 | Errico et al. |
| 5,904,683 | A | 5/1999 | Pohndorf et al. |
| 5,928,233 | A | 7/1999 | Apfelbaum et al. |
| 5,954,722 | A | 9/1999 | Bono |
| 5,964,762 | A | 10/1999 | Biedermann et al. |
| 5,964,763 | A | 10/1999 | Incavo et al. |
| 5,971,987 | A | 10/1999 | Huxel et al. |
| 5,976,140 | A | 11/1999 | Haas |
| 5,993,449 | A | 11/1999 | Schlapfer et al. |
| 6,010,503 | A | 1/2000 | Richelsoph et al. |
| 6,033,170 | A | 3/2000 | Gold |
| 6,039,740 | A | 3/2000 | Olerud |
| 6,059,786 | A | 5/2000 | Jackson |
| 6,117,135 | A | 9/2000 | Schlapfer |
| 6,139,316 | A | 10/2000 | Sachdeva et al. |
| 6,139,549 | A | 10/2000 | Keller |
| 6,152,927 | A | 11/2000 | Farris et al. |
| 6,187,005 | B1 | 2/2001 | Brace et al. |
| D440,311 | S | 4/2001 | Michelson |
| 6,224,602 | B1 | 5/2001 | Hayes |
| 6,235,034 | B1 | 5/2001 | Bray |
| 6,251,112 | B1 | 6/2001 | Jackson |
| 6,254,602 | B1 | 7/2001 | Justis |
| 6,273,888 | B1 | 8/2001 | Justis |
| 6,290,703 | B1 | 9/2001 | Ganem |
| D449,692 | S | 10/2001 | Michelson |
| 6,306,136 | B1 | 10/2001 | Baccelli |
| 6,309,391 | B1 | 10/2001 | Crandall et al. |
| 6,331,179 | B1 | 12/2001 | Freid et al. |
| 6,355,038 | B1 | 3/2002 | Pisharodi |
| 6,355,040 | B1 | 3/2002 | Richelsoph et al. |
| 6,361,258 | B1 | 3/2002 | Heesch |
| RE37,665 | E | 4/2002 | Ralph et al. |
| 6,368,320 | B1 | 4/2002 | Le Couedic et al. |
| 6,371,957 | B1 | 4/2002 | Amrein et al. |
| 6,379,357 | B1 | 4/2002 | Bernstein et al. |
| 6,402,752 | B2 | 6/2002 | Schaffler-Wachter et al. |
| 6,402,756 | B1 | 6/2002 | Ralph et al. |
| 6,454,769 | B2 | 9/2002 | Wagner et al. |
| 6,478,798 | B1 | 11/2002 | Howland |
| 6,524,315 | B1 | 2/2003 | Selvitelli et al. |
| 6,547,790 | B2 | 4/2003 | Harkey, III et al. |
| 6,565,565 | B1 | 5/2003 | Yuan et al. |
| 6,599,290 | B2 | 7/2003 | Bailey et al. |
| 6,602,255 | B1 | 8/2003 | Campbell et al. |
| 6,602,256 | B1 | 8/2003 | Hayes |
| 6,610,063 | B2 | 8/2003 | Kumar et al. |
| 6,623,485 | B2 | 9/2003 | Doubler et al. |
| 6,626,907 | B2 | 9/2003 | Campbell et al. |
| 6,645,207 | B2 | 11/2003 | Dixon et al. |
| 6,652,525 | B1 | 11/2003 | Assaker et al. |
| 6,663,631 | B2 | 12/2003 | Kuntz |
| 6,663,632 | B1 | 12/2003 | Frigg |
| 6,666,867 | B2 | 12/2003 | Ralph et al. |
| 6,679,883 | B2 | 1/2004 | Hawkes et al. |
| 6,695,846 | B2 | 2/2004 | Richelsoph et al. |
| 6,723,100 | B2 | 4/2004 | Biedermann et al. |
| 6,827,722 | B1 | 12/2004 | Schoenefeld |
| 6,830,571 | B2 | 12/2004 | Lenke et al. |
| 6,855,147 | B2 | 2/2005 | Harrington, Jr. |
| 6,884,243 | B2 | 4/2005 | Sellers |
| 6,885,243 | B2 | 4/2005 | Burstein et al. |
| 6,979,334 | B2 | 12/2005 | Dalton |
| 7,232,441 | B2 | 6/2007 | Altarac et al. |
| 7,303,563 | B2 | 12/2007 | Poyner et al. |
| 7,331,961 | B2 | 2/2008 | Abdou |
| 7,476,228 | B2 | 1/2009 | Abdou |
| 7,618,443 | B2 | 11/2009 | Abdou |
| 7,621,942 | B2 | 11/2009 | Piehl |
| 7,635,366 | B2 | 12/2009 | Abdou |
| 2001/0047172 | A1 | 11/2001 | Foley et al. |
| 2002/0016595 | A1 | 2/2002 | Michelson |
| 2002/0049446 | A1 | 4/2002 | Harkey, III et al. |
| 2002/0055741 | A1 | 5/2002 | Schlapfer et al. |
| 2002/0099386 | A1 | 7/2002 | Beger et al. |
| 2002/0111628 | A1 | 8/2002 | Ralph et al. |
| 2002/0143328 | A1 | 10/2002 | Shluzas et al. |
| 2002/0169453 | A1 | 11/2002 | Berger |
| 2002/0183755 | A1 | 12/2002 | Michelson et al. |
| 2002/0188296 | A1 | 12/2002 | Michelson |
| 2003/0078583 | A1 | 4/2003 | Biedermann et al. |
| 2003/0125741 | A1 | 7/2003 | Biedermann et al. |
| 2003/0153913 | A1 | 8/2003 | Altarac et al. |
| 2003/0167058 | A1 | 9/2003 | Shluzas |
| 2003/0199873 | A1 | 10/2003 | Richelsoph et al. |
| 2004/0133207 | A1 | 7/2004 | Abdou |
| 2004/0153070 | A1 | 8/2004 | Barker et al. |
| 2004/0204712 | A1 | 10/2004 | Kolb et al. |
| 2004/0204713 | A1 | 10/2004 | Abdou |
| 2004/0249380 | A1 | 12/2004 | Glascott |
| 2005/0004573 | A1 | 1/2005 | Abdou |
| 2005/0010227 | A1 | 1/2005 | Paul |
| 2005/0033296 | A1 | 2/2005 | Bono et al. |
| 2005/0033298 | A1 | 2/2005 | Hawkes et al. |
| 2005/0096653 | A1 | 5/2005 | Doubler et al. |
| 2005/0154390 | A1 | 7/2005 | Biedermann et al. |

(56) References Cited

U.S. PATENT DOCUMENTS

| | | |
|---|---|---|
| 2005/0177163 A1 | 8/2005 | Abdou |
| 2005/0216003 A1* | 9/2005 | Biedermann et al. ............ 606/61 |
| 2005/0228376 A1 | 10/2005 | Boomer et al. |
| 2005/0273120 A1 | 12/2005 | Abdou |
| 2005/0283153 A1 | 12/2005 | Poyner et al. |
| 2005/0288669 A1 | 12/2005 | Abdou et al. |
| 2006/0015181 A1 | 1/2006 | Elberg |
| 2006/0036252 A1 | 2/2006 | Baynham et al. |
| 2006/0074488 A1 | 4/2006 | Abdou |
| 2006/0085069 A1 | 4/2006 | Kim |
| 2006/0088398 A1 | 4/2006 | Lund |
| 2006/0089646 A1 | 4/2006 | Bonutti |
| 2006/0149240 A1 | 7/2006 | Jackson |
| 2006/0149278 A1 | 7/2006 | Abdou |
| 2006/0155278 A1 | 7/2006 | Warrick |
| 2006/0155284 A1 | 7/2006 | Doherty et al. |
| 2006/0161152 A1 | 7/2006 | Ensign et al. |
| 2006/0161154 A1 | 7/2006 | McAfee |
| 2006/0173456 A1 | 8/2006 | Hawkes et al. |
| 2006/0195089 A1 | 8/2006 | LeHuec et al. |
| 2006/0217710 A1 | 9/2006 | Abdou |
| 2006/0229610 A1 | 10/2006 | Piehl |
| 2006/0229615 A1 | 10/2006 | Abdou |
| 2006/0235387 A1 | 10/2006 | Peterman |
| 2006/0241614 A1 | 10/2006 | Bruneau et al. |
| 2007/0093817 A1 | 4/2007 | Barrus et al. |
| 2007/0093828 A1 | 4/2007 | Abdou |
| 2007/0093829 A1 | 4/2007 | Abdou |
| 2007/0106383 A1 | 5/2007 | Abdou |
| 2007/0118121 A1 | 5/2007 | Purcell et al. |
| 2007/0123867 A1 | 5/2007 | Kirschman |
| 2007/0123869 A1 | 5/2007 | Chin et al. |
| 2007/0123884 A1 | 5/2007 | Abdou |
| 2008/0027432 A1 | 1/2008 | Strauss et al. |
| 2008/0045963 A1 | 2/2008 | Abdou |
| 2008/0051783 A1 | 2/2008 | Null et al. |
| 2008/0058810 A1 | 3/2008 | Abdou |
| 2008/0147123 A1 | 6/2008 | Schermerhorn |
| 2008/0154308 A1 | 6/2008 | Sherman et al. |
| 2008/0312655 A1 | 12/2008 | Kirschman et al. |
| 2009/0163961 A1 | 6/2009 | Kirschman |
| 2009/0210007 A1 | 8/2009 | Levy et al. |
| 2009/0254125 A1 | 10/2009 | Predick |
| 2010/0076448 A1 | 3/2010 | Abdou |
| 2010/0121384 A1 | 5/2010 | Abdou |
| 2010/0241168 A1 | 9/2010 | Franck et al. |

FOREIGN PATENT DOCUMENTS

| | | |
|---|---|---|
| FR | 2856271 | 12/2004 |
| WO | WO 2004-032726 | 4/2004 |
| WO | WO 2004-062482 | 7/2004 |
| WO | WO 2004-093702 | 11/2004 |
| WO | WO 2005-122922 | 12/2005 |
| WO | WO 2006-041963 | 4/2006 |
| WO | WO 2006-045089 | 4/2006 |
| WO | WO 2006-058221 | 6/2006 |
| WO | WO 2006-089292 | 8/2006 |
| WO | WO 2006-096756 | 9/2006 |
| WO | WO 2007-041648 | 4/2007 |
| WO | WO 2007-044705 | 4/2007 |
| WO | WO 2007-044836 | 4/2007 |
| WO | WO 2007-056516 | 5/2007 |
| WO | WO 2007-059207 | 5/2007 |

OTHER PUBLICATIONS

Derwent English Abstract for French Patent Publication FR 2781359, published Jan. 28, 2000, entitled: "Osteosynthesis frame for spinal surgery has rod with clamps to hold cross bars with anchor screws". Accession No. 9867555. cited by applicant.

Derwent English Abstract for French Patent Publication FR 2856271, published Dec. 24, 2004, Osteo-synthesis vertebral column plate, has connection head integrated with plate and movable in three directions of space so as to adapt itself to connection rod, and including opening to facilitate introduction of rod. Accession No. 14694557. cited by applicant.

Scott Yerby, Ph.D., C. Corey Scott, MS, Nathan J. Evans, MS, Katie L. Messing, MS, and Dennis R. Carter, Ph.D., "The Effect of Cutting Flute Design on the Insertion and Pullout Properties of Self-tapping Bone Screws"; pp. 1-2; Jul. 2, 2002. cited by applicant.

Richard N.W. Wohns, M.D. and Roger D. Robinett, M.D., "Day Surgery for Anterior Cervical Microdiskectomy: Experience with 75 Cases", pp. 1-3, Jul. 11, 2002. cited by applicant.

* cited by examiner

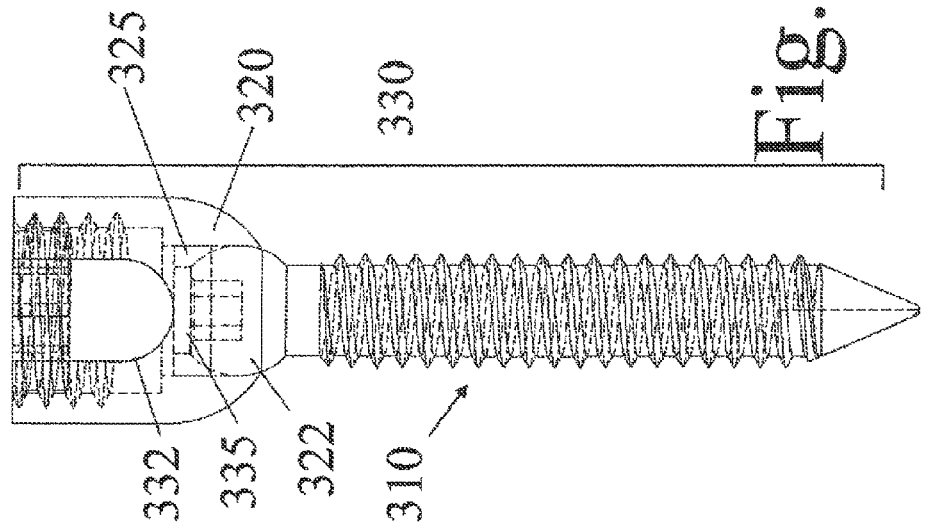
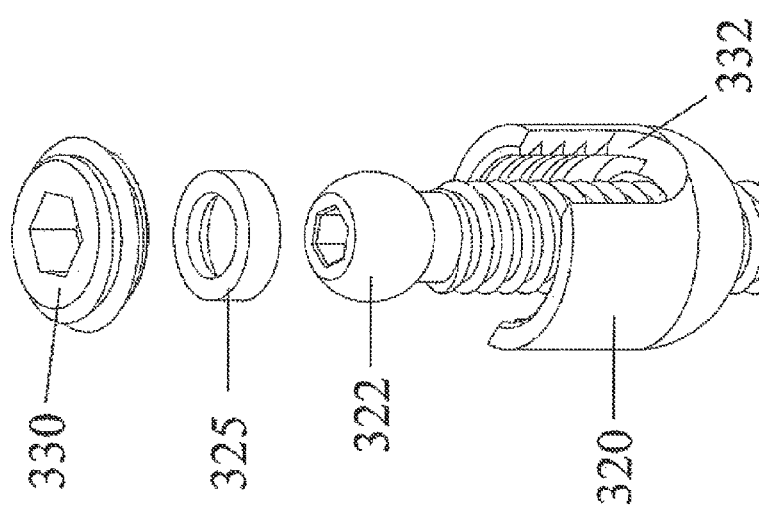

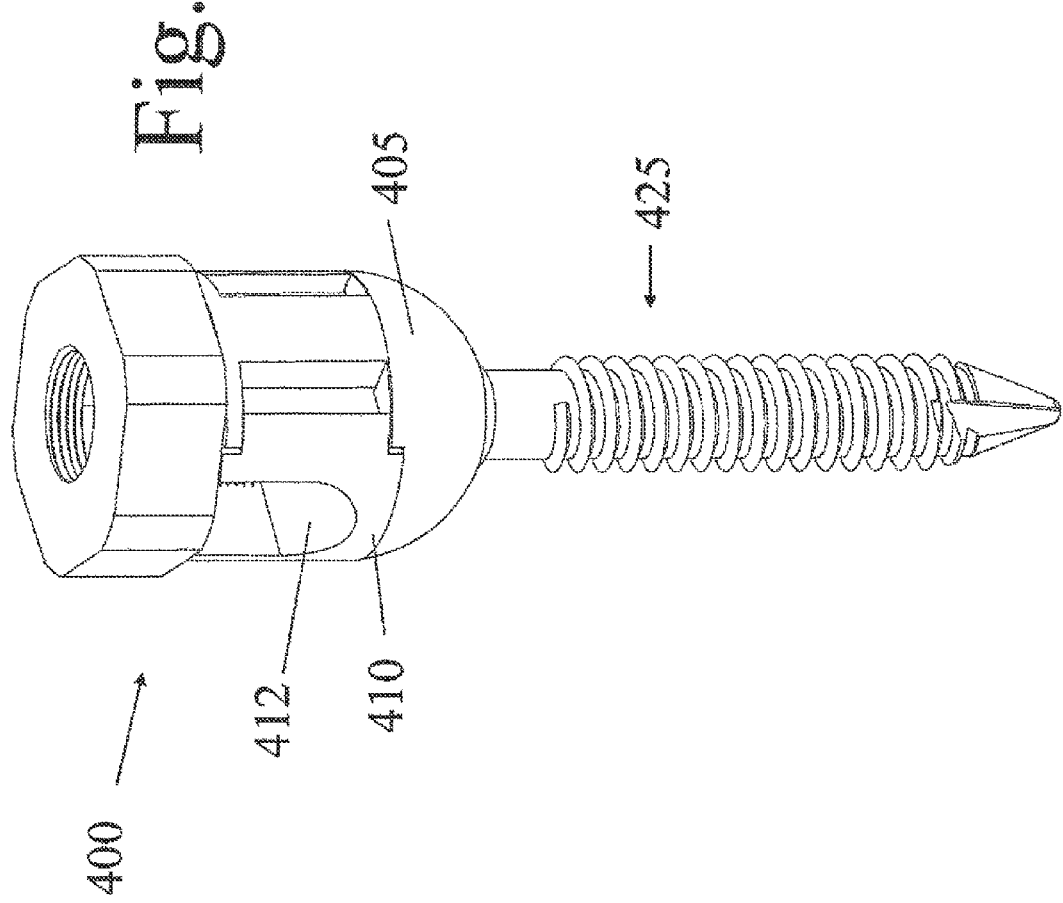

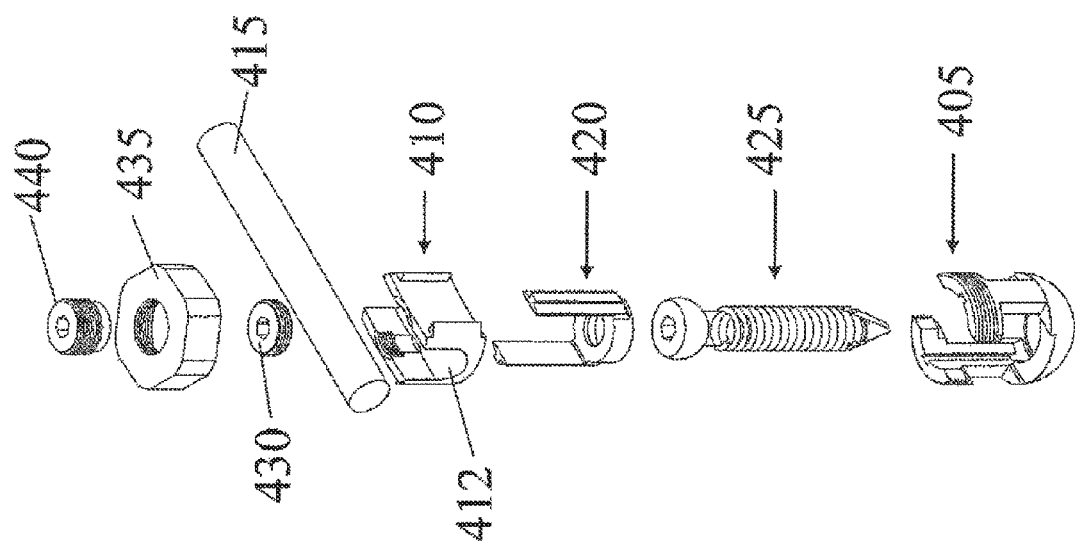

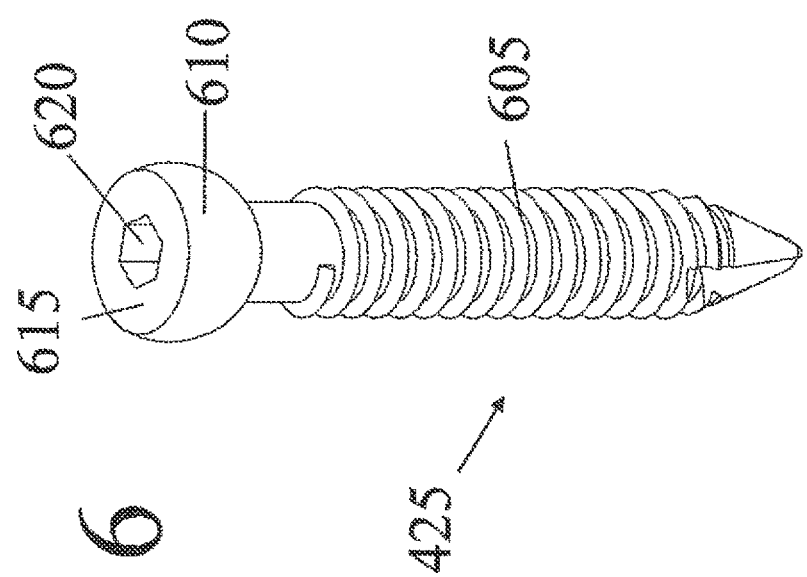

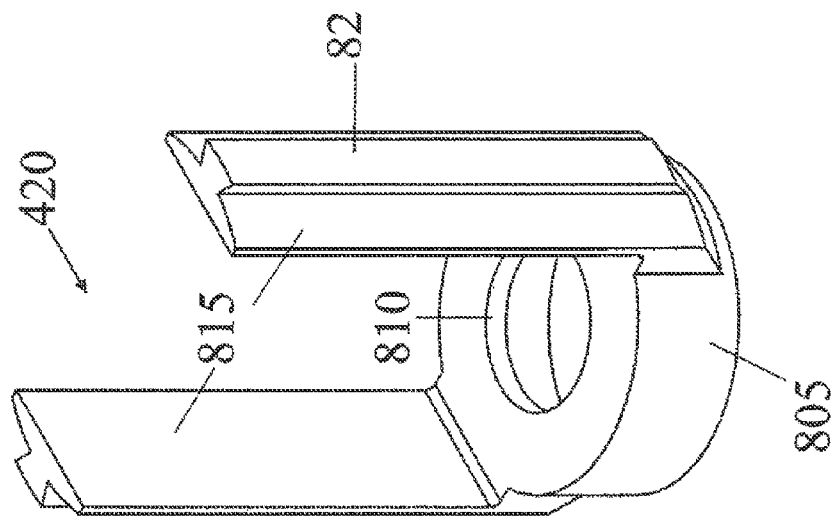
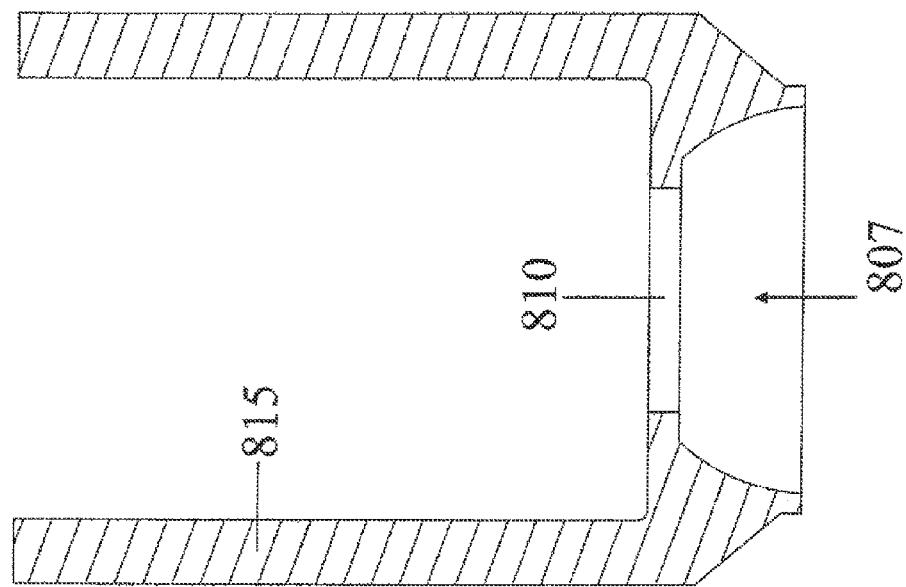

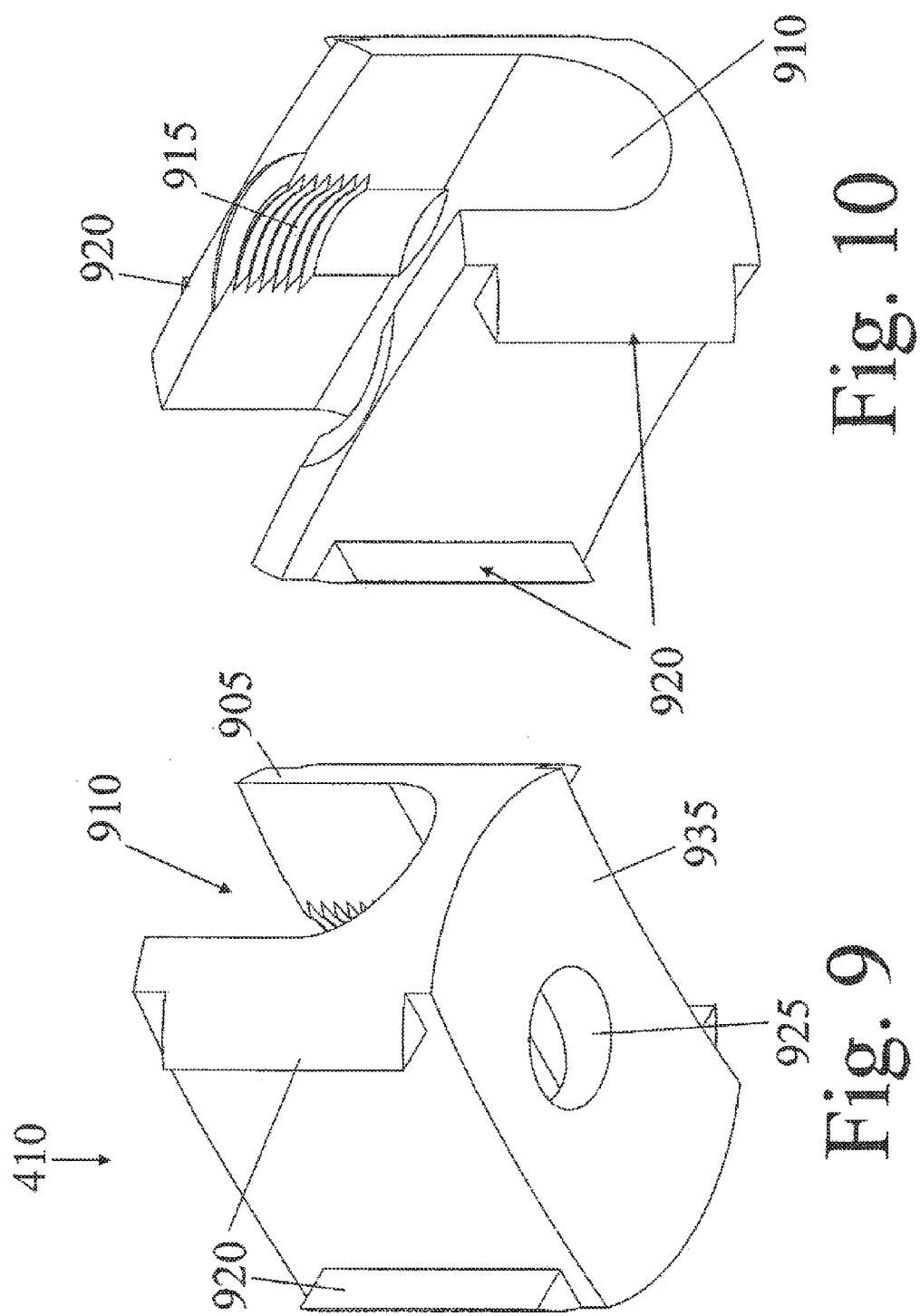

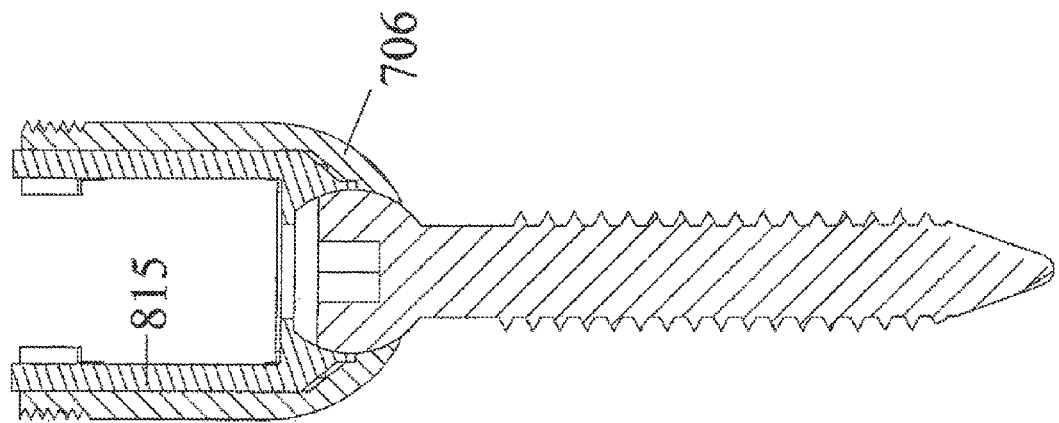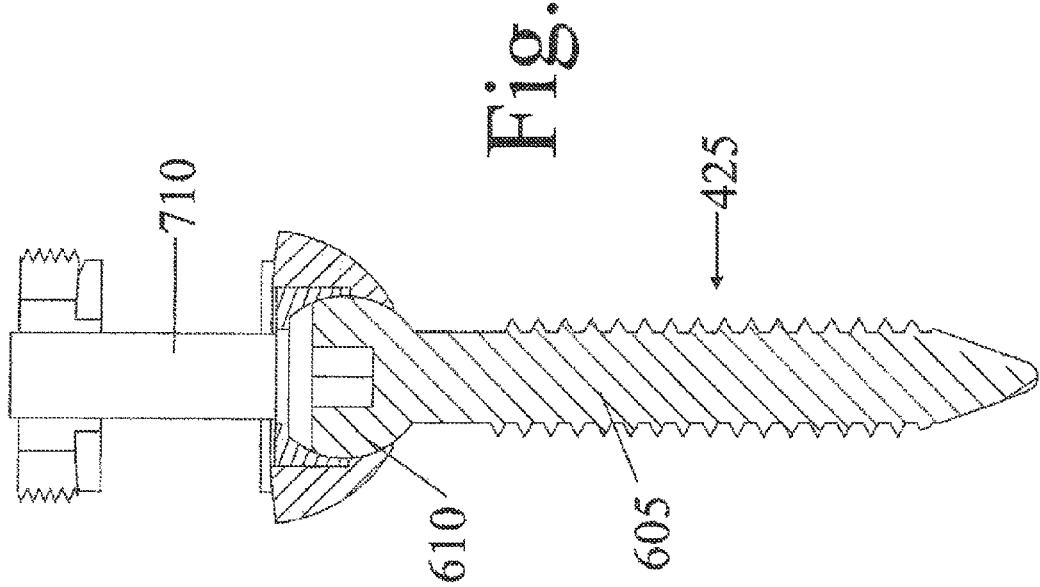
Fig. 13

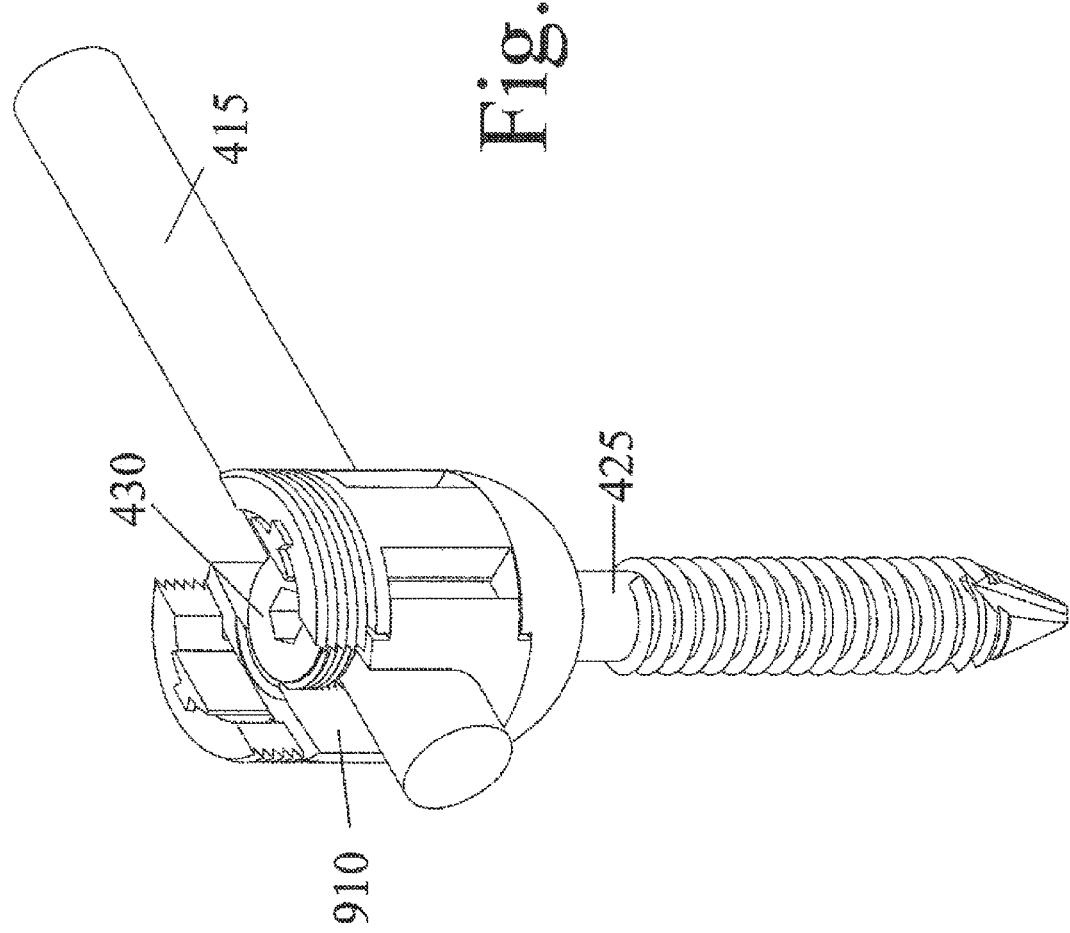

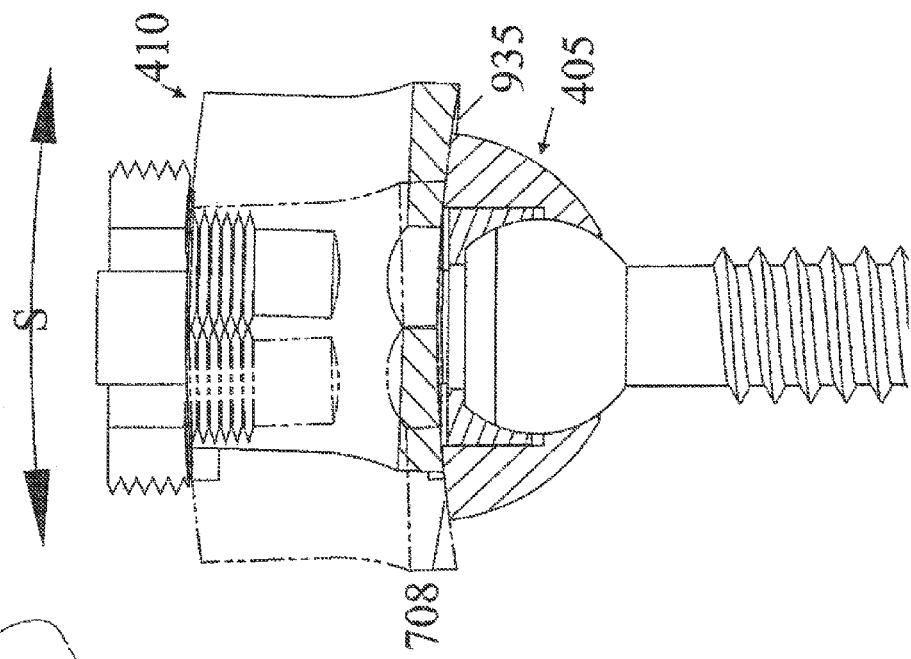
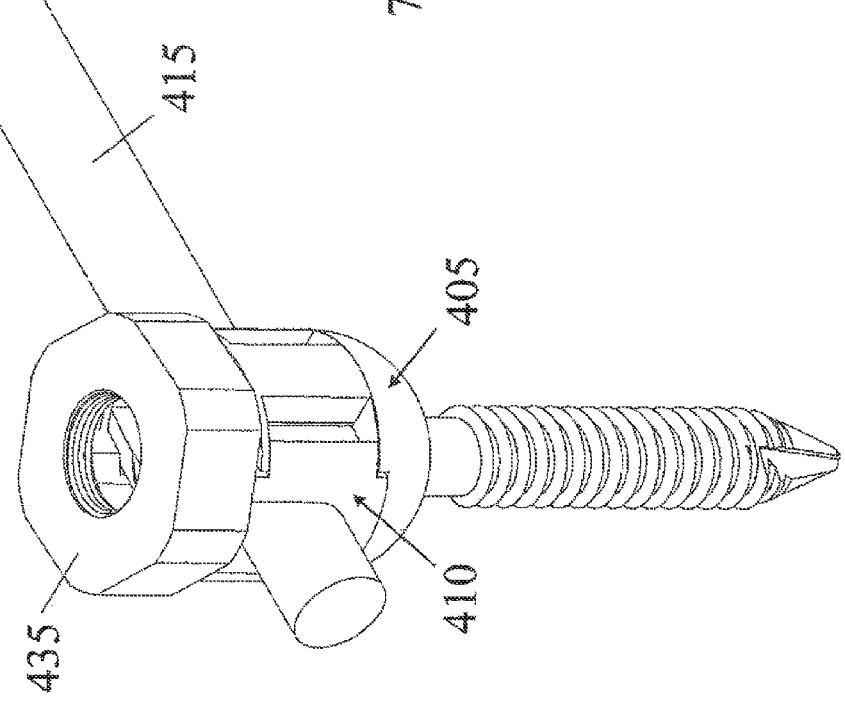

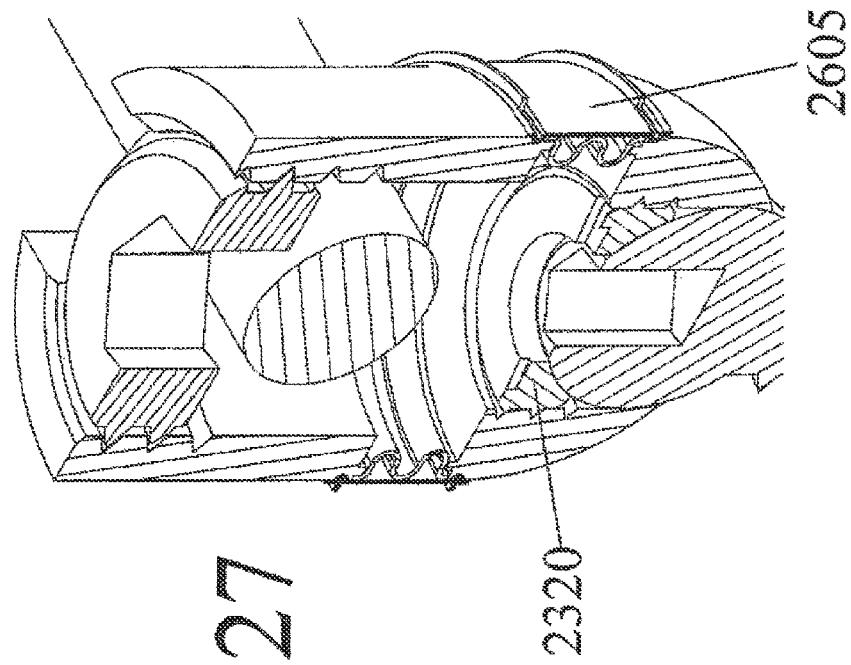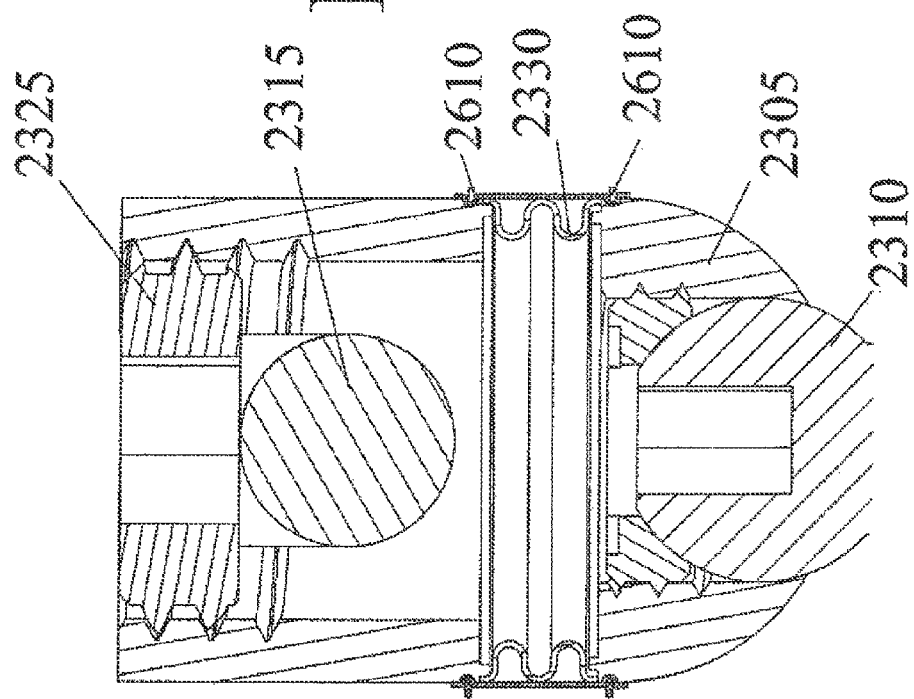
Fig. 27

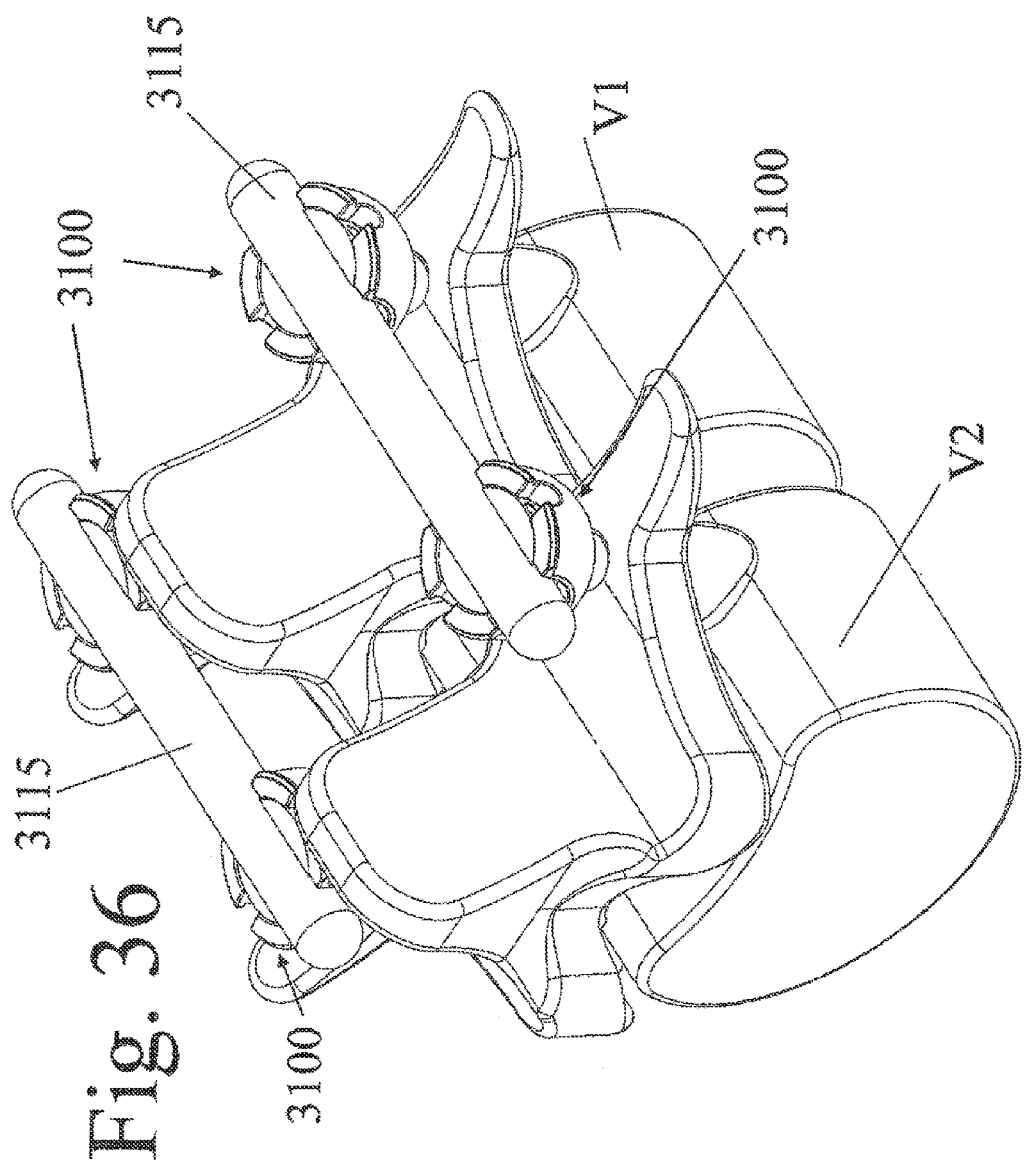

DEVICES AND METHODS FOR DYNAMIC FIXATION OF SKELETAL STRUCTURE

REFERENCE TO PRIORITY DOCUMENT

This application is a divisional of and claims priority to co-owned U.S. patent application Ser. No. 13/846,696 filed on Mar. 18, 2013 of the same title, which is a divisional of and claims priority to U.S. patent application Ser. No. 12/882,117 filed on Sep. 14, 2010, of the same title and issued as U.S. Pat. No. 8,398,689 on Mar. 19, 2013 which is a continuation of and claims priority to co-owned U.S. patent application Ser. No. 11/360,038, filed Feb. 21, 2006 issued as U.S. Pat. No. 7,862,588 on Jan. 4, 2011 of the same title, which claims priority of the following U.S. Provisional Patent Applications: (1) U.S. Provisional Patent Application Ser. No. 60/749,719, flied Dec. 12, 2005; (2) U.S. Provisional Patent Application Ser. No. 60/731,690, filed Oct. 31, 2005; and (3) U.S. Provisional Patent Application Ser. No. 60/654,602, filed Feb. 18, 2005. Priority of the aforementioned filing dates is hereby claimed, and the disclosures of the Patent Applications are hereby incorporated by reference in their entirety.

BACKGROUND

The present disclosure relates to methods and devices that permit stabilization of the bony elements of the skeleton. The methods and devices permit adjustment and maintenance of the spatial relationship(s) between neighboring bones. Depending on the specifics of the design, the motion between skeletal segments may be increased, reduced, returned to a normal physiology state or modulated in any desired manner.

Surgical reconstruction of the bony skeleton is a common procedure in current medical practice. Regardless of the anatomical region or the specifics of the reconstructive procedure, many surgeons employ an implantable device that can adjust, align and maintain the spatial relationship(s) between adjacent bones.

Whether from degenerative disease, traumatic disruption, infection or neoplastic invasion, alteration in the anatomical relationships between the spinal vertebras can cause significant pain, deformity and disability. Spinal disease is a major health problem in the industrialized world and the surgical treatment of spinal pathology is an evolving discipline. The traditional surgical treatment of abnormal vertebral motion has been the complete immobilization and bony fusion of the involved spinal segment. An extensive array of surgical techniques and implantable devices has been formulated to achieve complete immobilization.

The growing experience with spinal fusion has shed light on the long-term, consequences of vertebral immobilization. It is now accepted that fusion of a specific spinal level will increase the load on, and the rate of degeneration of, the spinal segments immediately above and below the fused level. As the number of spinal fusion operations have increased, so have the number of patients who require extension of their fusion to the adjacent, degenerating levels. The second procedure necessitates re-dissection through the prior, scarred operative field and carries significantly greater risk than the initial procedure while providing a reduced probability of pain relief. Further, extension of the fusion will increase the load on the motion segments that now lie at either end of the fusion construct and will accelerate the rate of degeneration at those levels. Thus, spinal fusion begets additional, future fusion surgery.

In view of the proceeding, there is a growing recognition that segmental spinal fusion and complete immobilization is an inadequate solution to abnormal spinal motion. Correction of the abnormal movement and preservation of spinal mobility is a more intuitive and rational treatment option. It is appropriate to employ motion correction in the initial treatment plan and reserve complete immobilization and fusion for those patients with advanced motion abnormalities that can not be corrected.

SUMMARY

Disclosed are dynamic bone screws that permit correction and control of the movement between adjacent bones. The screws can be used pursuant to an implantation protocol that provides ease of use as well as a safe and familiar surgical approach. The bone screws and bone screw assemblies described herein permit flexible stabilization of the spine.

Complete immobilization of the spinal segment is most commonly accomplished by screw fixation of the bony elements while the bone graft matures into a solid fusion. In order to preserve motion, a bone graft is not used with the bone screw assemblies described herein. In addition, the disclosed bone screw assemblies are adapted to permit movement of the spinal segments to which the assemblies are attached, while still providing stabilization of the spinal segments. Thus, the disclosed bone screw assemblies are adapted to stabilize spinal segments, but still move or articulate in response to the imposition of stress caused by the relative displacement of the spinal segments.

Bone fixation is accomplished by the attachment of a first bone screw assembly to one bone and a second bone screw assembly to a second bone. The two screw assemblies are interconnected using a rigid rod so that the bone segments are immobilized relative to each other. The disclosed screw assemblies include a screw that attaches onto the bone, a housing member that connects and inter-locks the bone screw to the rod, and one or more locking members that permit immobilization of various components of the assembly relative to one another while still permitting some relative movement. In the devices disclosed herein, a rigid interconnecting rod is preserved and various embodiments of a dynamic screw assembly are shown.

In one embodiment, a dynamic screw assembly is created by removing or not employing a locking element of the bone screw assembly. In this way, a housing member of the bone screw assembly serves to place the bone screw in proximity to a rod but does not immobilize the bone screw and the rod relative to one another.

In another embodiment, a head of the bone screw resides within a housing member and, within defined limits, the spatial relationship between the screw shaft and the housing member can vary. A saddle member resides within a segment of the housing member. A surface or element of the saddle member movably engages a complimentary surface or element of the housing member. This permits movement of the saddle member within the housing member. Characteristics of movement are defined by the characteristics of complimentary surfaces or elements between the housing member and the saddle member that permit relative movement therebetween. An inner aspect of the saddle member accommodates a rod that can be used to connect the assembly to other bone screw assemblies. A first locking nut permits immobilization of the rod relative to the saddle member and a second locking nut is used to immobilize the bone screw relative to the housing member. In this way, a dynamic screw assembly is formed by providing movement between the saddle member and the housing member. Further, the addition of a third locking nut can transform the dynamic screw assembly into a rigid one.

In another embodiment, the bone screw locks onto one segment of the housing member and the rod attaches onto another segment of that member. The housing member contains a movable interconnection between the two attachment points. In this way, a dynamic screw assembly is created that provides movement within the housing member.

In another embodiment, a secondary moving element or surface is placed between the head of the bone screw and the central housing member. When the assembly is locked, both the rod and the secondary moving surface are immobilized relative to the housing member. However, the bone screw remains mobile within the confines of the secondary moving surface. Thus, a dynamic screw assembly is created that provides movement between the bone screw and housing member.

In another embodiment, the bone screw contains a movable intermediate segment between the screw shaft that engages the bone and the screw head that lies within the central housing member. In this way, a dynamic screw assembly is created that provides movement within the bone screw itself.

In another embodiment, a malleable member surrounds the rod and screw within the confines of a rigid housing. In this way, a dynamic screw assembly is created that provides relative movement between the rod and screw head.

The bone screws described herein form a dynamic screw assembly while maintaining use of a rigid rod between different screw assemblies. While describe as separate embodiments, the various mechanisms may be used in combinations to produce additional screw assemblies that have specific desired properties (such as an axis of rotation within a specified spatial location).

In one aspect, there is disclosed a bone fixation assembly, comprising: an elongate rod; a bone fixation member adapted to be secured to a spinal segment; a housing assembly having a first portion adapted to be removably attached to the rod in a manner that immobilizes the rod relative to the first portion, the housing assembly also having a second portion adapted to be removably attached to the fixation member to place the rod and the fixation member in proximity; wherein at least a portion of the bone fixation assembly can articulate while the rod is immobilized relative to the housing assembly to permit the fixation member to move from an initial orientation to a different orientation relative to the rod in response to application of a load on the bone fixation assembly, and wherein the fixation member is automatically urged toward the initial configuration when the load is removed.

In another aspect, there is disclosed a bone fixation assembly, comprising: an elongate rod; a bone screw adapted to be secured to a spinal segment; a housing assembly that receives the rod and that receives the screw so as to place the rod in proximity to the screw; a locking member that couples to the housing assembly to immobilize the rod relative to the housing assembly; wherein at least a portion of the bone fixation assembly can articulate to permit the rod and the screw to move from an initial spatial relationship to a second spatial relationship, and wherein at least a portion of the bone fixation assembly urges the rod and the screw back toward the initial spatial relationship upon movement away from the initial spatial relationship.

In another aspect, there is disclosed a bone fixation assembly, comprising: a bone screw adapted to engage a spinal segment; a housing movably coupled to the bone-engaging member, the housing being adapted to seat a fixation rod; and a looking member adapted to mate to the housing to lock the fixation rod in a fixed position relative to the housing; wherein the bone fixation assembly permits at least limited relative displacement between the bone screw and the fixation rod while the fixation rod is immobilized relative to the housing, the bone fixation assembly being reformed from an initial configuration to a different configuration in response to an imposition of stress on the bone screw assembly, and automatically recovering toward the initial configuration when the stress is removed.

In another aspect, there is disclosed a bone fixation assembly comprising: an elongate rod; a bone fixation member adapted to be secured to a spinal segment; and a housing assembly having: an inner housing having a slot receives the rod in a manner that permits immobilization of the rod relative to inner housing; and an outer housing having a seat that receives a head of the bone fixation member such that a shank of the bone fixation member extends outwardly from the outer housing; wherein the inner housing movably mounts within the outer housing to place the rod and the fixation member in proximity such that the fixation member can move from an initial orientation to a second orientation relative to the rod in response to application of a load on the bone fixation assembly, and wherein the fixation member is automatically urged toward the initial configuration when the load is removed.

In another aspect, there is disclosed a bone fixation assembly, comprising: a spinal rod; a housing assembly having a channel adapted to receive the spinal rod; a locking member adapted to immobilize the rod relative to the housing; and a bone screw extending from the housing assembly and adapted to engage a spinal segment; wherein at least a portion of the bone fixation assembly includes an articulation region that elastically articulates to permit relative movement between the rod and the screw.

In another aspect, there is disclosed a bone fixation assembly, comprising: an elongate rod; a bone fixation member adapted to be secured to a spinal segment; a housing assembly including an outer housing with a slot that receives the rod, the outer housing further including a seat, and wherein the housing assembly further includes an inner housing positioned in the seat, wherein the inner housing defines a socket in which a head of the bone fixation member is movably positioned; and a locking member adapted to immobilize the rod and the inner housing relative to the outer housing while the head is movable within the socket.

In another aspect, there is disclosed a bone fixation assembly, comprising: an elongate rod; a bone fixation member adapted to be secured to a spinal segment; and a housing assembly including an outer housing and at least one locking member positioned within the outer housing and adapted to receive the rod, the housing assembly further comprising a rotational member rotatably positioned within the locking member and the outer housing, the rotational member forming a socket in which a head of the fixation member is rotatably positioned; wherein the rod can be pressed downward into the locking member to immobilize the rod in the locking-member and the locking member in the housing and further immobilize the rotational member relative to the locking member while permitting rotatable movement of the head of the fixation member within the socket.

In another aspect, there is disclosed a method of stabilizing the spine, comprising: providing a fixation assembly including a housing, a bone screw, and a rod; securing the fixation assembly to a spine segment such that the bone screw is fixated within the spine segment; and locking the fixation assembly such that the rod is immobilized relative to the housing while the bone screw can move from an initial orientation to a different orientation relative to the rod in response to application of a load on the bone fixation assembly, and wherein the bone screw is automatically urged toward the initial configuration when the load is removed These and other features will become more apparent from the following description and certain modifications thereof when taken with the accompanying drawings.

BRIEF DESCRIPTION OF THE DRAWINGS

FIGS. 3A and 3B show an exploded view and a cross-sectional assembled view of another embodiment of a non-rigid bone screw assembly.

FIG. 4 shows an assembled view of another embodiment of a bone screw assembly that permits movement of the screw, rod, and/or housing relative to one another prior to complete locking of the device.

FIG. 5 shows an exploded view of the assembly of FIG. 4.

FIG. 6 shows a perspective view of a bone screw of the assembly of FIGS. 4 and 5.

FIG. 8A shows a perspective view of a locking member of the assembly of FIGS. 4 and 5.

FIG. 8B shows a cross-sectional view of the locking member.

FIGS. 9 and 10 show a perspective views of a saddle member of the assembly of FIGS. 4 and 5.

FIG. 13 shows a cross-sectional view of the assembly in the partially assembled state.

FIG. 17 shows the assembly with the rod positioned within the saddle member and the inner locking nut positioned to immobilize the rod in place relative to the saddle member.

FIG. 18A shows the assembly with the outer locking nut engaged with the outer housing.

FIG. 18B shows a cross-sectional view of the assembly with the inner saddle member positioned within the outer housing.

FIG. 27 shows a cross-sectional view of the assembly of FIG. 26.

FIG. 36 shows the screw assembly of FIG. 32 placed into the pedicle portion of a vertebra.

DETAILED DESCRIPTION

Figure 1:
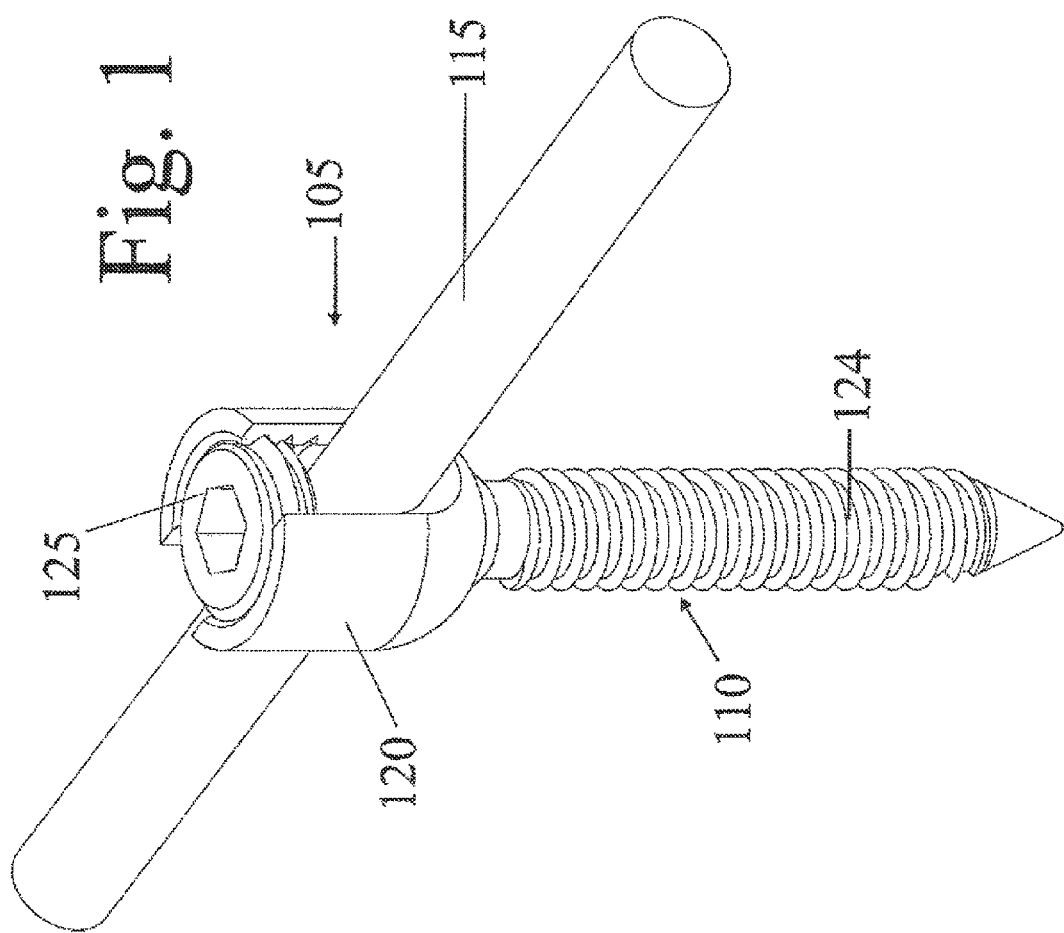
FIG. 1 shows a conventional, rigid fixation screw assembly.

Disclosed are methods and devices for fixating a device to a skeletal structure, such as to a spinal motion segment (also referred to as a spinal segment), such as a vertebra. The disclosed bone screw assemblies are adapted to secure an elongate rod (or any other type of elongate element or stabilizer for use in conjunction with a spinal fixation system) to a bone fixation device, such as a bone screw or a bone hook that attaches to a spinal segment. The disclosed bone screw assemblies are adapted to secure the rod to the fixation device while permitting at least some movement or articulation of the rod relative to the fixation device, such as in response to the imposition of stress caused by the relative displacement of the attached spinal segments. The assemblies can include one or more locking members that can be actuated or adjusted to vary the level and/or type of relative movement between the rod and the fixation device and to also completely immobilize the rod relative to the fixation device if such immobilization is desired. The assemblies can be partially or entirely manufactured of one or more materials that enable such relative movement, as described below.

The disclosed dynamic assemblies permit spine stabilization in that a first spinal segment can be attached to a second spinal segment using rod-interconnected bone screw assemblies, wherein each assembly is attached to its respective spinal segments via a bone fastener. The bone screw assemblies can include at least one dynamic bone screw assembly of the type described herein. Bone screws are the most commonly used fasteners in spinal stabilization and the devices disclosed in this application will illustrate dynamic assemblies that utilize bone screw fasteners. However, it is understood that hooks, clamps, cables, or any suitable fastener may be alternatively used. The stabilization is flexible in that each assembly permits at least some relative movement between the rod and the screw thereby permits the spinal segment to move-relative to the rod. The interconnected bone screw assemblies permit at least some control over relative movement between the vertebral segments, while permitting movement of the spinal segments relative to one another.

The screw assemblies described herein can vary in structure and it should be appreciated that the disclosure is not limited to the particular structures described herein. Some embodiments include a housing that couples to a rod or other type of longitudinal element for use in conjunction with a spinal fixation system. One or more locking members are used to immobilize the housing relative to the rod. The housing also couples to a bone screw that fixedly attaches to a spinal segment. One or more locking members are used to couple the bone screw relative to the housing. The structural arrangement and/or materials of manufacture of the components of the screw assemblies are adapted to permit relative movement between the rod and the screw, between the rod and the housing, between the screw and the housing, within the screw, and combinations thereof.

In some implementations, the housing can be manufactured of two or more components that attach to one another in a manner that permits limited, relative movement between the housing components. The rod can be fixedly attached to one or more of the components while the screw is fixedly attached to one or more separate components of the housing. Because the components can move relative to one another, the rod and the screw can move relative to one another while still being commonly attached to the housing. The screw, housing, and/or intermediate components can also be manufactured of a material that is deformable or flexible to permit relative movement via deformation of the components themselves.

In this regard, the components of the screw assembly can be entirely or partially manufactured of a shape-memory material that exhibits superelastic (also known as pseudoelastic) characteristics. Shape memory materials (typically shape memory alloys (SMAs)) are materials that can be deformed at one temperature, but when heated or cooled, the materials return to their original, pre-deformed shape. Thus, the material "memorizes" a previous shape Shape memory materials undergo a reversible transformation from one crystal phase to another over a particular temperature range. Above this temperature range, the material exists as austenite, which has a rigid crystal structure. The shape of a component while in the austenite phase is typically-referred to as the memory shape. A low temperature phase, martensite, is soft and can be deformed from its original shape without causing any permanent deformation. Once deformed, martensitic material will remain in this deformed shape indefinitely. When heated later, the material transforms to the high temperature phase and returns to its memory shape. The transformation between martensitic and austenitic phases can occur as a result of a change of temperature or as a result of the imposition of stress on the material. In this regard, a thermoelastic martensitic transformation has occurred if the transformation occurs in response to a change in temperature. If the martensitic transformation occurs as a result of the imposition of stress, then a stress-induced martensitic transformation has occurred.

Shape memory materials can exhibit superelasticity wherein a small force induces considerable deformation but when the force is removed, the material automatically recovers its original shape without the need for heating. The superelastic phenomena occurs when stress is applied to a shape memory material at a temperature slightly higher than the temperature at which the material begins to transform into austenite. When stressed, the material first deforms elastically up to the yield point of the material. When further stress is applied to the material, it begins to transform into stress-induced martensite. When the stress is removed, the material transforms back into austenite and the material returns to its original, memorized shape.

A nickel-titanium alloy know as Nitinol is an example of a shape-memory material. Nitinol is advantageous for use in the screw assemblies described herein, as Nitinol can be programmed to undergo a stress-induced martensitic transformation at about normal human body temperature (i.e., at about 35-40 degrees Celsius).

An article entitled Shape Memory Effect and Super-Elasticity in Ni—Ti Alloys, Titanium and Zirconium, Vol. 30, No. 4, October 1982 (which is incorporated herein by reference), by Yuichi Suzuki, provides details regarding the superelasticity. The disclosed screw assemblies can be at least partially manufactured of a shape memory material that exhibits superelastic characteristics or behavior at about human body temperature.

Figure 2:
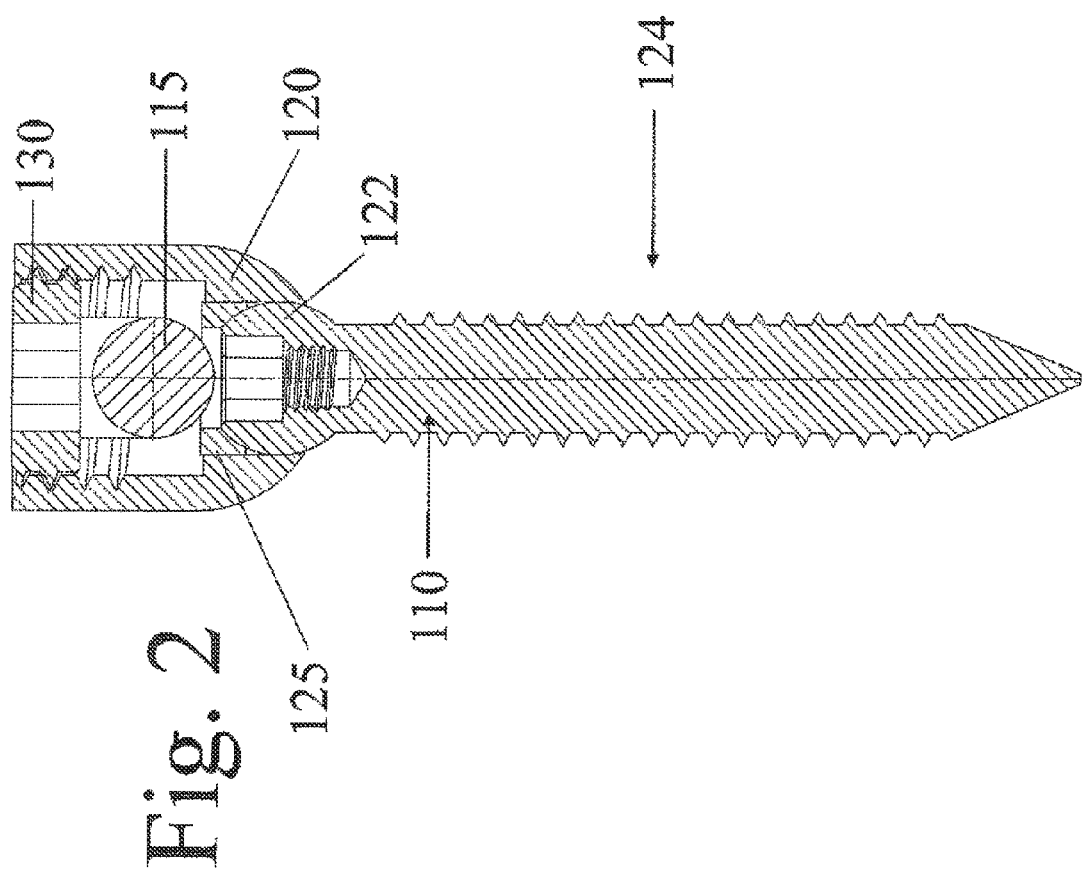
FIG. 2 shows a cross-sectional view of the assembly in a locked position.

FIG. 1 shows a conventional, rigid fixation screw assembly. FIG. 2 shows a cross-sectional view of the assembly 105 in a locked position. The assembly 105 includes a fixation member comprised of a bone screw 110, an elongate rod 115, and a housing 120 that couples to both the bone screw 110 and the rod 115. The housing 120 has a slot that is sized to receive the rod 115. The assembly of FIGS. 1 and 2 is rigid in that the bone screw is completely immobilized relative to the housing 120 and the rod 115 when a locking member is tightened onto the rod. Thus, no relative movement between the rod and the bone screw is permitted when the locking member is tightened onto the rod.

An internal bore in the housing 120 is sized to receive the screw 110. In this regard, a head 122 of the bone screw 110 sits within a seat in the housing 120 such that an anchoring portion (such as a shank portion 124 or a hook) of the bone screw 110 protrudes downwardly out of the housing 120. A locking member 125 its above the head 122 and below the rod 115 in the housing 120. A locking nut 130 can be advanced downward into the housing 120 to force the rod 115 downwardly against the locking member 125 and compress the screw 110 against the inner aspect of the housing 110. When locking nut 130 is fully advanced, the assembly becomes rigid such that the screw 110 is completely immobilized relative to the housing 120 and the rod 115.

There are now described various embodiments of bone screw assemblies that are non-rigid, such that there is at least some level of relative movement between the rod 115, the housing 120 and/or the bone screw 110 while still placing the rod in proximity to the bone screw. The assemblies can also be rigid upon the actuation of locking members.

In one embodiment, one or more of the components of the assembly of FIGS. 1 and 2 are manufactured of a deformable or flexible material. The material can be a shape memory material, for example. Because the material is deformable, at least some level of movement of the components relative to one another is enabled. For example, the saddle 125 can be manufactured of a material that deforms upon the satisfaction of deformation criteria, such as upon the application of a threshold level force. If such a threshold level of force is applied to the saddle 122 via the screw, then the screw can be rotated relative to the housing 120. Other components of the assembly 105 can also be manufactured of a deformable material.

Thus, the components of the assemblies described herein can be manufactured of a shape memory material. The material has a memorized shape wherein the screw is placed in a first orientation relative to the rod. Upon the imposition of stress or a load to the material, the material transforms to a different shape that places the screw in a different orientation relative to the rod. If the material is reshaped or deformed while at a temperature above the material's transformation temperature, the material automatically recovers toward its memorized shape when the stress is removed. In one embodiment, a screw assembly is attached to a spinal segment while at least one component (such as the housing, rod, screw, or portion thereof) of the assembly is in a substantially unstressed initial configuration where virtually all of the shape memory material is in an austenitic state. Upon the imposition of stress onto a portion of the assembly (which can be caused by relative movement between the spinal segments), at least a portion of the material is transformed into reversible stress-induced martensite. Upon the reduction or removal of stress, at least a portion of the material is transformed back into austenite.

Any of the components of the bone screw assemblies described herein can be at least partially formed of a shape-memory material that exhibits pseudoelastic characteristics or behavior at about human body temperature. As mentioned, Nitinol is an example of a material that can be programmed to undergo a stress-induced martensitic transformation at about normal human body temperature (i.e., at about 35-40 degrees Celsius). It should be appreciated that any of the embodiments described herein can be at least partially manufactured of a deformable material.

FIGS. 3A and 3B show an exploded view and a cross-sectional assembled view of another embodiment of a non-rigid bone, screw assembly 305. The assembly 305 includes a bone screw 310, a housing 320, a saddle 325, and a locking nut 330. The saddle 325 is interposed between a head of the screw 310 and the rod when the assembly 305 is assembled. For clarity of illustration, the rod is not shown in FIGS. 3A and 3B, although the rod is adapted to be received within a slot 332 in the housing 320.

The saddle 325 is dimensioned such that the rod 315 does not directly compress against the saddle 325 when the rod is pressed fully downward into the slot 332 in the housing 320. Rather, the rod 315 abuts the bottom edge of the slot 332. The bottom edge is above the level of the top surface of the saddle 325 such that the rod 315 does not press downward against the saddle 325 when the rod is pressing against the bottom edge of the slot 332. Full advancement of the locking nut 330 locks or immobilizes the rod 315 relative to the housing 320, but still permits movement of the screw 310 relative to the housing 320. That is, the head 322 of the screw 310 can rotate within the housing 310 when the locking nut 330 is fully advanced downward against the rod 115. When the head 322 rotates, the orientation of the longitudinal axis of the screw 310 varies.

With reference to FIG. 3B, a space 335 is located between the head 322 of the screw 310 and the rod when the rod is positioned in the housing 320. The space 335 can be loaded with a material that resists movement of the screw, but still permits some movement when a load of sufficient force is applied to the screw. Thus, the space can be fitted, for example, with springs, Belleville washers, fluids, elastic materials, magnets or any know mechanism that can be adapted to resist movement of the screw 310 within the housing 320. In this manner, the screw 310 can move relative to the housing 310, but only if a force is applied to the screw wherein the force is of sufficient magnitude to overcome the movement-resistant material or structure within the space 335.

This screw assembly has a neutral position wherein longitudinal axis of the housing is perpendicular to the plane atop the head of the screw, as shown in FIG. 3B. In the neutral position, the net force acting upon the screw is zero. However, when the screw is moved outside of the neutral position (such that the plane atop of the screw head is no longer perpendicular or substantially perpendicular to the longitudinal axis of the housing), the material placed in space 335 will exert a net force on the head of the screw and return the screw to the neutral position. In this embodiment, the neutral position is pre-determined. That is, there is a pre-determined relationship between the longitudinal axis of the housing and plane atop the screw had (such as perpendicular). That relationship is a function of screw design and cannot be changed by the surgeon at the time of screw placement.

At implantation, the screw assembly of the current embodiment will be in the neutral position. In order to connect several non-linear screw assemblies with a single rod, the housing of one or more assemblies must be taken out of the neutral position. This maneuver will necessarily cause the bone screws of the assemblies in the non-neutral position to apply significant load onto the attached bones. Since it is sometimes undesirable to place a load on the vertebral bones at the time of screw implantation, other embodiments are illustrated that will obviate this feature. In those embodiments, the housing and bone screw may be placed in any desired position relative to one another before the assembly's neutral position is set. That is, the neutral position is not pre-determined in those embodiments.

FIG. 4 shows an assembled view of another embodiment of a bone screw assembly 400 that permits movement of the screw, rod, and/or housing relative to one another prior to complete locking of the device. FIG. 5 shows an exploded view of the assembly of FIG. 4. The assembly of FIGS. 4 and 5 includes a housing that is formed of several components that can move or articulate relative to one another. The rod can be immobilized relative to a first component while the screw can be immobilized relative to a second component of the housing. Because the first and second components are movable relative to one another, the rod and screw can move relative to one another while still being coupled to one another.

The assembly includes a housing comprised of an outer housing 405 and an inner saddle member 410 having a slot 412 for receiving a rod 415 (FIG. 5). A locking member 420 (FIG. 5) fits within the outer housing 405 above a bone screw 425. The bone screw 425 sits within a seat in the bottom of the outer housing 405 such that a shank of the screw 425 extends outwardly from the outer housing 405. An inner locking nut 430 interfaces with the saddle member 410 for providing a downward load on the rod 415 for securing the rod relative to the saddle member 410, as described below. An Outer locking nut 435 interfaces with the outer housing 405 for locking the assembly together, as described below. A central locking nut 440 engages a central, threaded bore within the outer locking nut 435. The locking nuts 430, 435, and 440 can provide various combinations of immobilization of the rod 115, screw 425, and housing relative to one another.

FIG. 6 shows a perspective view of the bone screw 425. The bone screw 425 includes a shank 605 that extends from a head 610. The head 610 has an upper surface in which is disposed a drive connector such as a cavity 620 that is sized and shaped to receive a tool for driving the screw 425 into bone. The cavity 620 can be, for example, hexagonal shaped to receive a hex drive for engaging and rotating the screw 425.

Figure 7A:
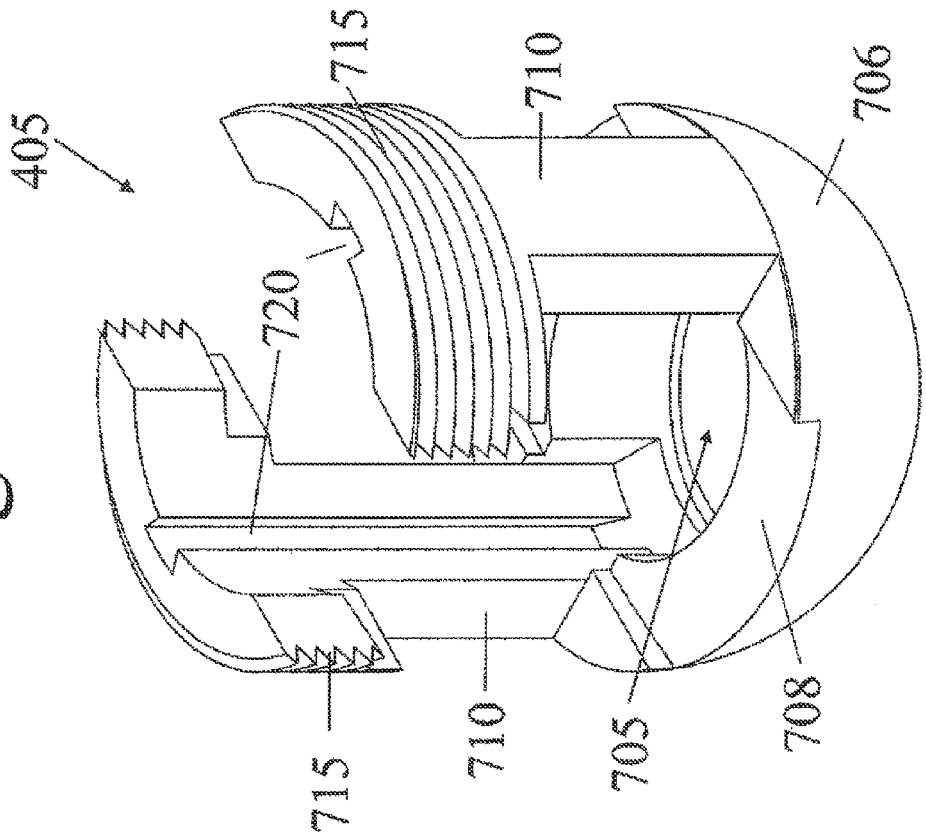
FIG. 7A shows a perspective view of an outer housing of the assembly of FIGS. 4 and 5.
Figure 7B:
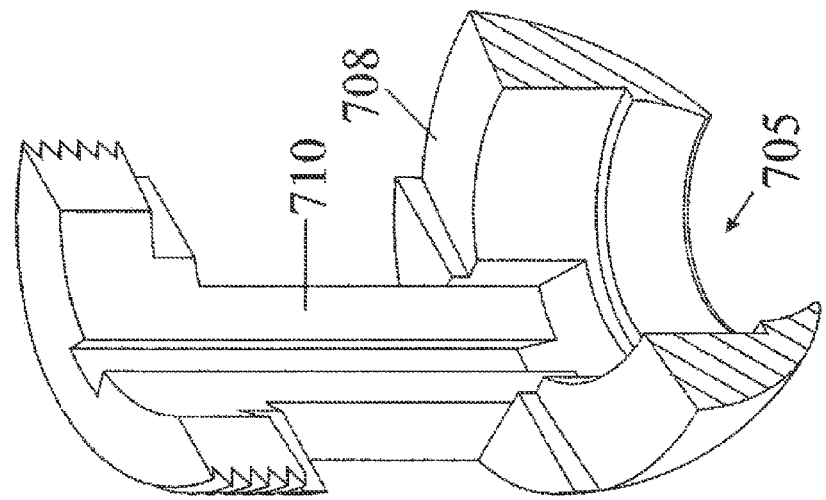
FIG. 7B shows a cross-sectional, perspective view of the outer housing.

FIG. 7A shows a perspective view of the outer housing 405. FIG. 7B shows a cross-sectional, perspective view of the outer housing 405. A central bore extends through the outer housing for receipt of the bone screw 425. A seat 705 is located within a base region 706 of the outer housing 405 for receiving the head 610 of the screw 425. The base region 706 has a pair of upper surfaces 708 that face a region of the saddle member 410 in the assembled device. The upper surfaces 708 can be convex along two dimensions or can have any contour.

A pair of opposed extensions 710 extend upwardly from the base region 706 and flare outwardly to form into threaded regions 715 that interface with the outer locking nut 435 (FIG. 5). Each of the extensions 710 has an inner surface that includes an elongate slot 720 that slidingly engages a complementary-shaped extension of the locking member 420, as described in detail below.

FIG. 8A shows a perspective view of the locking member 420 of the assembly of FIGS. 4 and 5. FIG. 8B shows a cross-sectional view of the locking member 420. As mentioned, the locking member 420 is positioned within the outer housing 425 above the screw 425 in the assembled device. A base 805 has a hole 810 extending therethrough wherein the hole 810 is located directly above the drive cavity 620 of the bone screw 425 when the device is assembled. As shown in the cross-sectional view of FIG. 8B, a bottom region of the base 805 forms a cavity 807 that is positioned immediately above the head 610 of the screw 524 in the assembled device.

A pair of opposed extensions 815 extend upwardly from the base 805. Each extension has a rail 820 positioned on an outer surface of the extension. The extensions 815 are positioned relative to one another such that they can fit in-between the extensions 710 (FIGS. 7A and 7B) of the outer housing 405. In addition, the rails 820 are sized, shaped and positioned to slidingly engage the slots 720 (FIGS. 7A and 7B) of the extensions 710 of the outer housing 405, as described in more detail below.

Figure 11:
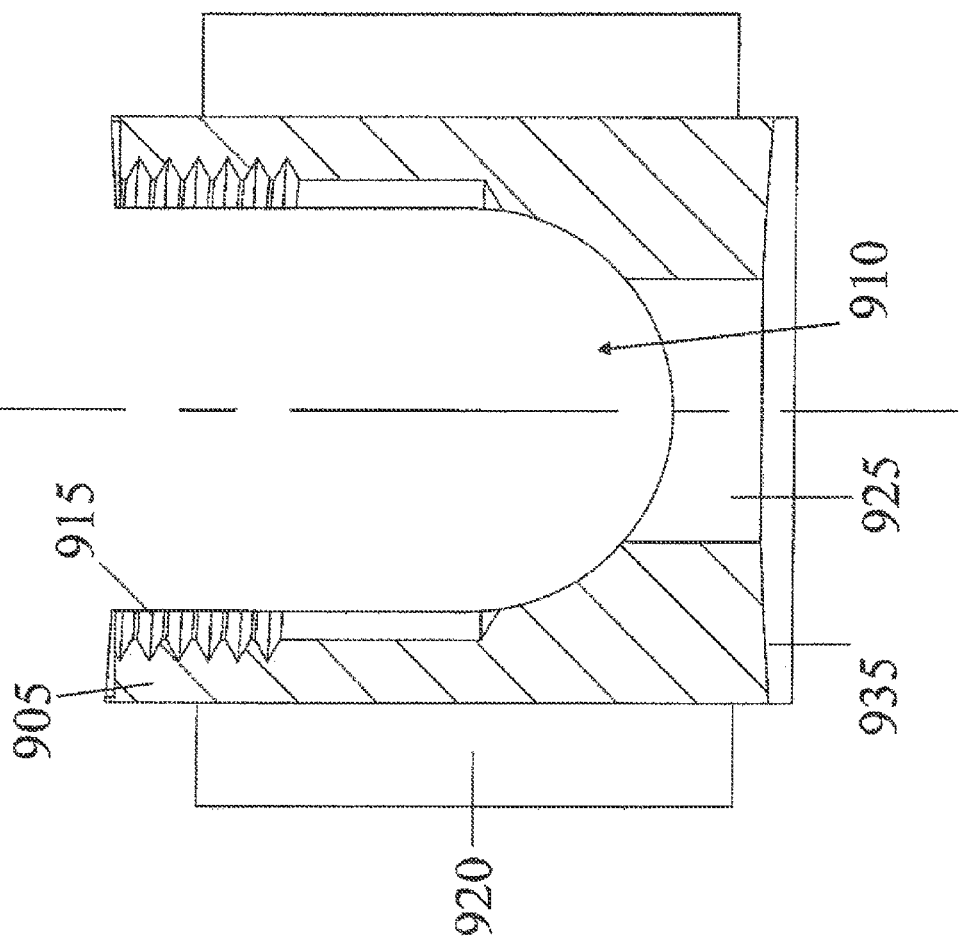
FIG. 11 shows a cross-sectional view of the saddle member.

FIGS. 9 and 10 show a perspective views of the saddle member 410. FIG. 11 shows a cross-sectional view of the saddle member 410. The saddle member 410 has a pair of extensions 905 that form a rod channel 910 therebetween wherein the channel 910 is adapted to receive the rod 415. A threaded engagement region 915 on the inner surface of the extensions 905 is adapted to interface with the inner locking nut 430 (FIG. 5). The outer aspect of each extension 905 includes a pair of protrusions 920 that function to limit the amount of movement of the saddle 410 relative to the outer housing 405 of the assembled device, as described in detail below. As best shown in FIGS. 9 and 11, a borehole 925 extends through a base of the saddle member 410.

With reference to FIGS. 9-11, the saddle member 410 has a bottom surface 935 that is positioned adjacent to the upper surfaces 708 (FIGS. 7A, 7B) of the outer housing 405 in the assembled device. The bottom surface 935 can have a contour that is selected to permit relative movement of the saddle member 410 and the outer housing 405 such that the bottom surface 935 can slide relative to the upper surfaces 708, as described below. For example, the bottom surface 935 can be concave along two dimensions. The saddle member 410 is dimensioned to fit within the outer housing 405. In this regard, the saddle member 410 is at least slightly undersized relative to the space between the extensions 710 of the outer housing 405 to permit some travel or movement between the saddle member and the outer housing in the assembled device.

Figure 12:
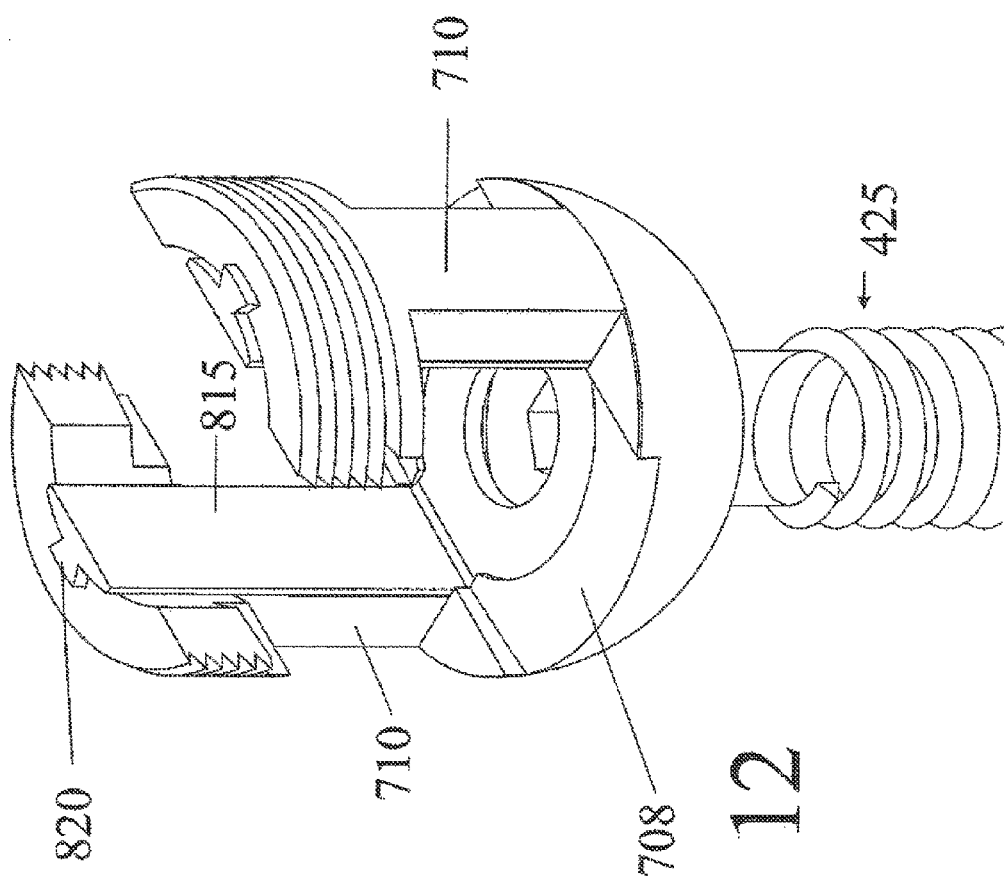
FIG. 12 shows a perspective view of the assembly in a partially assembled state.

FIG. 12 shows a perspective view of the assembly 400 in a partially assembled state with the screw 425 and the locking member 420 engaged with the outer housing 405. FIG. 13 shows a cross-sectional view of the assembly 400 in the partially assembled state. The head 610 of the screw 425 is positioned within the seat in the base region 706 of the outer housing 405 such that the shank 605 extends through the bore in the outer housing 405. The head 610 is free to move within the seat. That is, the head 610 can rotate within the seat in a ball and socket manner.

With reference to FIGS. 12 and 13, the locking member 420 is positioned within the outer housing 405 such that the rails 820 are slidable positioned within the slots 720 of the extensions 710 on the outer housing 405. The extensions 815 on the locking member 420 have a height such that upper edges of the extensions 815 extend past the upper edges of the extensions 710 of the outer housing 405. In this manner, the upper edges of the extensions 815 can be pressed downwardly so that the locking member 420 exerts a locking force on the head 610 of the screw 425 to immobilize the screw 425 relative to the outer housing 405, as described in detail below. The outer locking nut 435 can be used to press the upper edges of the extensions 815, as described below. The borehole 810 (FIG. 12) is positioned above the drive cavity 620 in the head 610 of the screw 425 to permit a hex drive to be engaged with the drive cavity 620.

Figure 14:
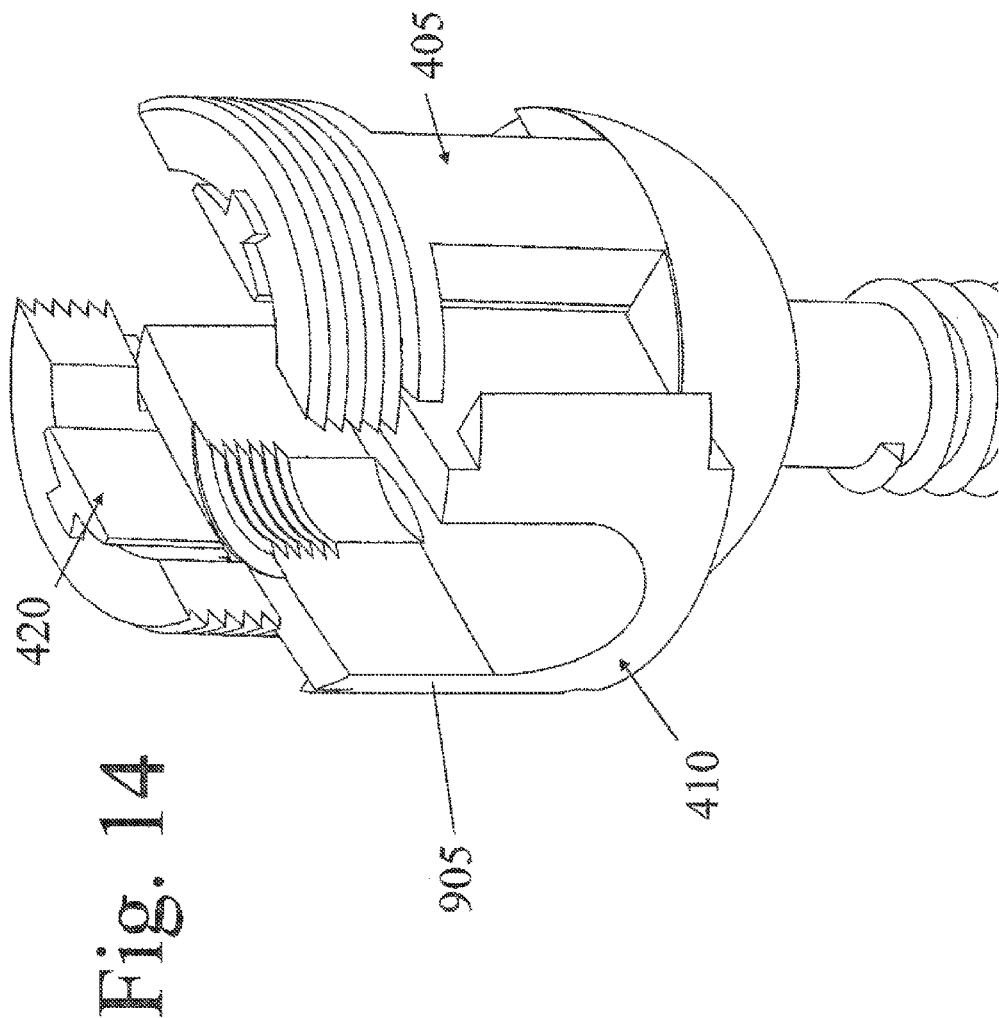
FIG. 14 shows a perspective view of the assembly with the saddle member being inserted into the outer housing.
Figure 15:
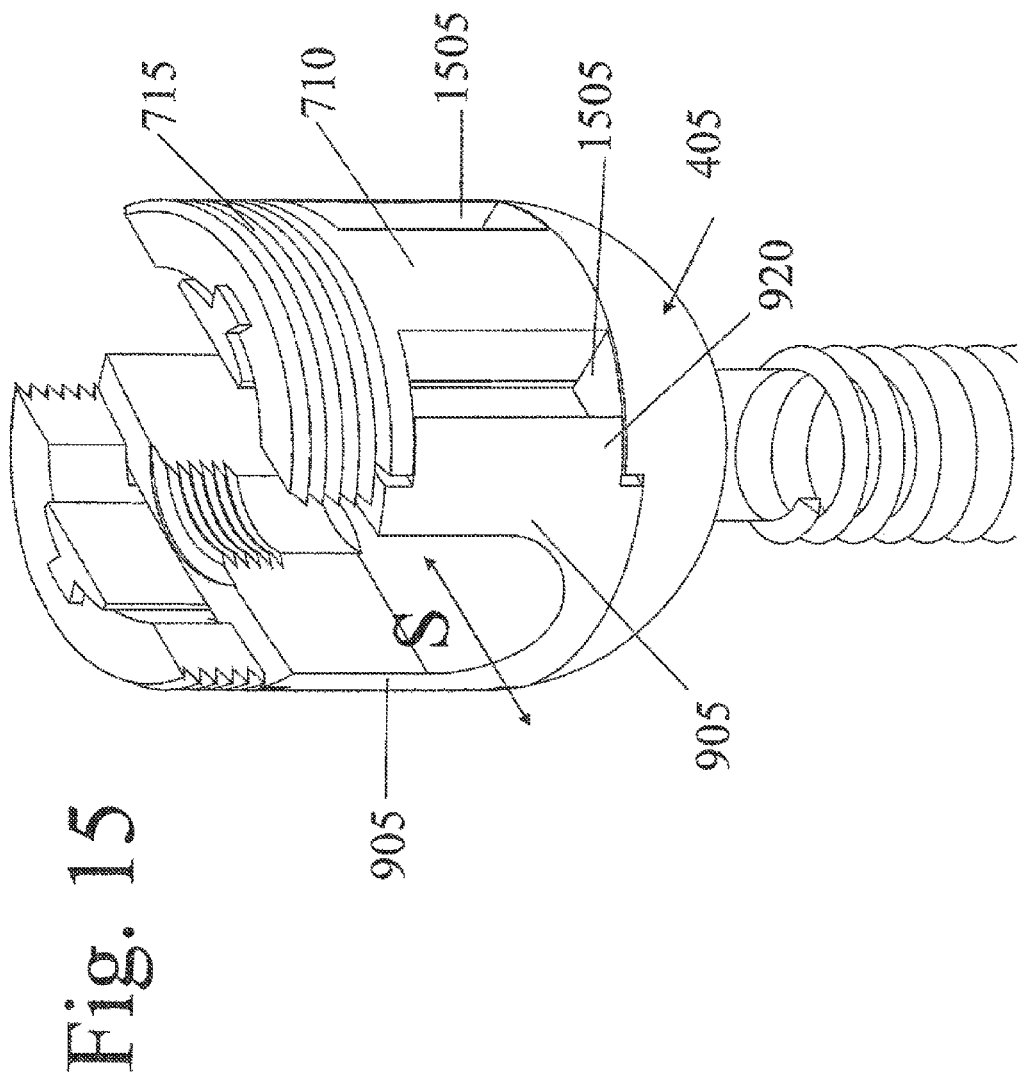
FIG. 15 shows the assembly with the saddle member fully inserted into the outer housing.
Figure 16:
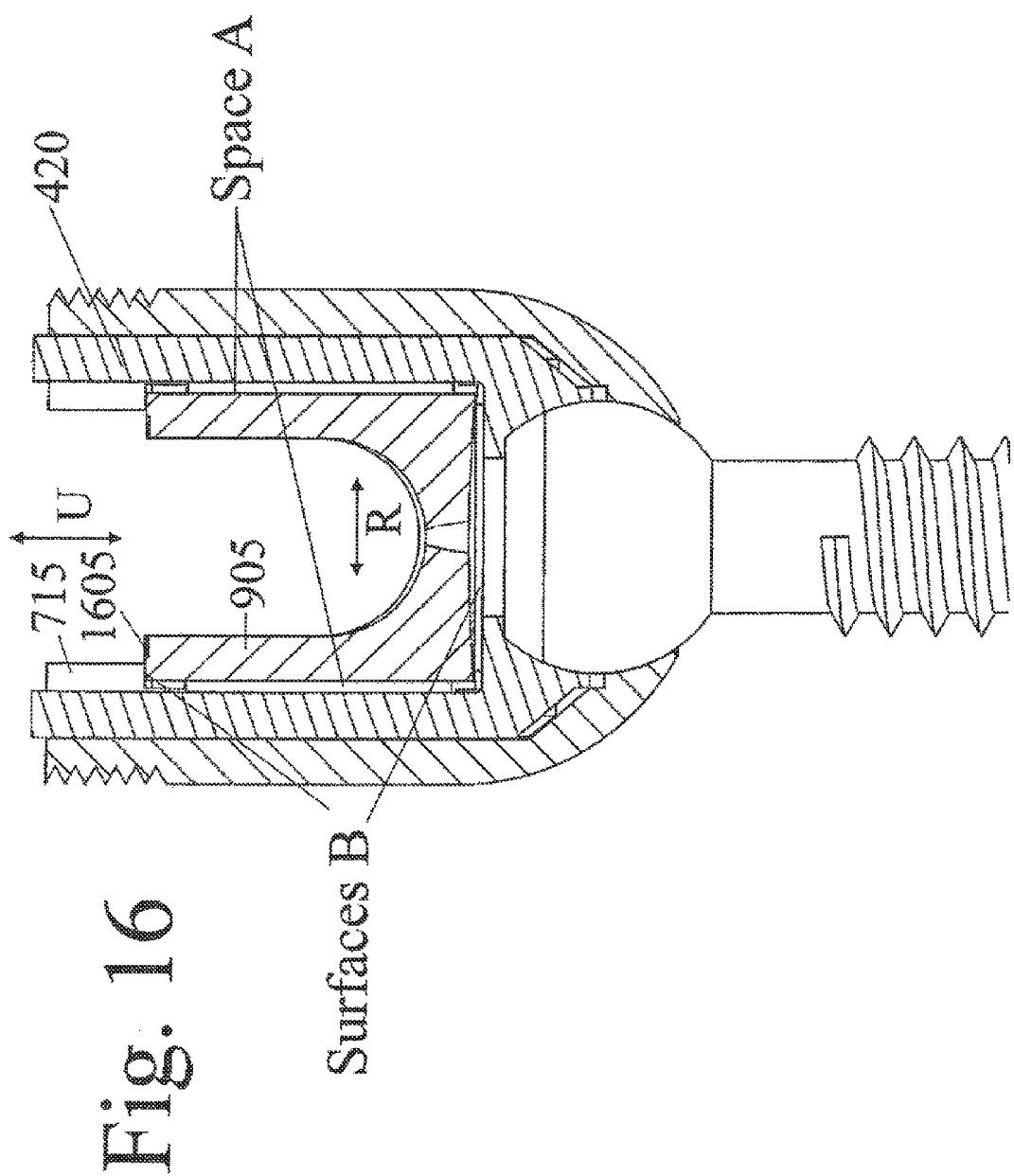
FIG. 16 shows a cross-sectional view of the assembly.

FIG. 14 shows a perspective view of the assembly with the inner saddle member 410 deviated to one side within housing 405. FIG. 15 shows the assembly with the saddle member 410 in the midline ("neutral") position within outer housing 405. FIG. 16 shows a cross-sectional view of the assembly. The saddle member 410 slides into the space between the extensions 710 on the outer housing 405 and the locking member 420. As best shown in FIG. 16, the upper edges of the extensions 905 on the saddle member 410 are positioned below the lower edges of the widened threaded region 715 of the outer housing 405 with a small space B positioned therebetween. A small space B is positioned between the lower surface of the saddle member 410 and the surface 708 of the outer housing 405.

With reference to FIG. 16, a space A exists between the sides of the saddle member 410 and the inner sides of the outer housing 405 and locking member 420. With reference to FIG. 15, a space 1505 is located between the protrusions 920 and the extensions 710. The size of the space is limited by the size of the protrusions 920. The spaces A, B, and 1505 permit the saddle member 410 to have some play or movement relative to the outer housing. 405 when the saddle member 410 is positioned in the outer housing 405.

It should be appreciated that the size and shape of the spaces can be varied. Moreover, the saddle member 410 can be sized and shaped relative to the outer housing 405 such that other spaces are formed. At least one purpose of the spaces is to permit relative movement between the saddle member 410 and the outer housing 405 and this can be accomplished in various manners. Thus, the screw can be moved from a first orientation (such as the neutral position) to a second orientation while the rod is immobilized relative to the inner member 410.

Any of the spaces, A, B, or 1505 can be fitted with an elastic or deformable material or other mechanism, such as a spring, that resists such movement of the saddle member 410 within the outer housing 405. In this way, the device will resist movement to either side and will return to a predetermined position, such as a mid-line position, after an applied force has dissipated.

FIG. 17 shows the assembly 400 with the rod 415 positioned within the saddle member 410 and the inner locking nut 430 positioned to immobilize the rod 415 in place relative to the saddle member 410. As mentioned, the rod 415 sits within the channel 910 of the saddle member 410. The inner locking nut 430 can be threaded downwardly into the saddle member 410 so as to provided a downward force on the rod 415 and lock the rod 415 relative to the saddle member. When fully seated, the inner locking nut 430 locks the rod 415 within inner saddle member 410. At the stage shown in FIG. 17, the rod 415 is immobilized relative to the saddle member 410, while the screw 425 can still rotate within the seat in the outer housing 405. Thus, both the screw and the rod are attached to the outer housing but the screw and the rod can have relative movement with respect to one another.

FIG. 18A shows the assembly 400 with the outer locking nut 435 engaged with the outer housing 405. The outer locking nut 435 has internal threads that engage the threaded region 715 (FIG. 7A) of the outer housing 405. The outer locking nut 435 can be threaded downward onto the outer housing 405. As this occurs, the outer locking nut 435 provides a downward force on the upper edge of the extensions 815 (FIG. 13) of the locking member 420. As mentioned, the upper edges of the locking member extend upwardly past the upper edges of the outer housing 405. The outer locking nut 435 thus presses the locking member 420 downward, which in turn presses downward on the head of the screw 425. The head of the screw 425 is pressed downward into the seat 705 (FIGS. 7A and 7B) of the housing 405 with a force sufficient to immobilize the screw 425 within the seat of the outer housing.

At this stage, the bone screw 425 is immobilized relative to the outer housing 405 due the outer locking nut 435 and the locking member 420 pressing downward on the screw head. The inter-connecting rod 115 is locked or immobilized relative to the inner saddle member 410 due to the downward force provided by the inner locking member 430 (FIG. 17). However, the inner saddle member 410 can move relative to the outer housing 405 due to the spaces A and B (FIG. 16) and the space 1505 (FIG. 15) between the inner saddle member 410 and the outer housing 405. Thus, the rod 115 can move relative to the screw 425 while both components are still coupled to the housing.

With reference to FIG. 15, the inner saddle member 410 can slidably move within the outer housing 405 along a direction aligned with axis S wherein the amount movement is limited by the interplay between the protrusions 920 and the extensions 710. This type of movement is represented in FIG. 18B, which shows a cross-sectional view of the assembly with the inner saddle member 410 positioned within the outer housing 405. The inner saddle member 410 is represented in solid lines at a first position and in phantom lines at a second position after sliding from right to left in FIG. 18B. The bottom surface 935 of the inner saddle member 410 slides along the upper surface 708, of the outer housing 405. As mentioned, the surfaces can be contoured such that the inner saddle member slides along an axis S that has a predetermined radius of curvature. This can be advantageous during flexion and extension of the attached spinal segments, as the radius of curvature of the axis S can be selected to provide motion along the physiologic axis of rotation of the spinal segments.

With reference now to FIG. 16, the inner saddle member 410 can also move up and down along axis U and side-to-side along axis R relative to the outer housing 405 due to the spaces A and B. Some rotational and/or pivoting movement of the inner saddle member 1505 relative to the outer housing 405 is also possible. Thus, movement of the inner saddle member relative to the outer housing provides the dynamic quality of the device as such movement permits the rod to move relative to the screw.

Figure 19:
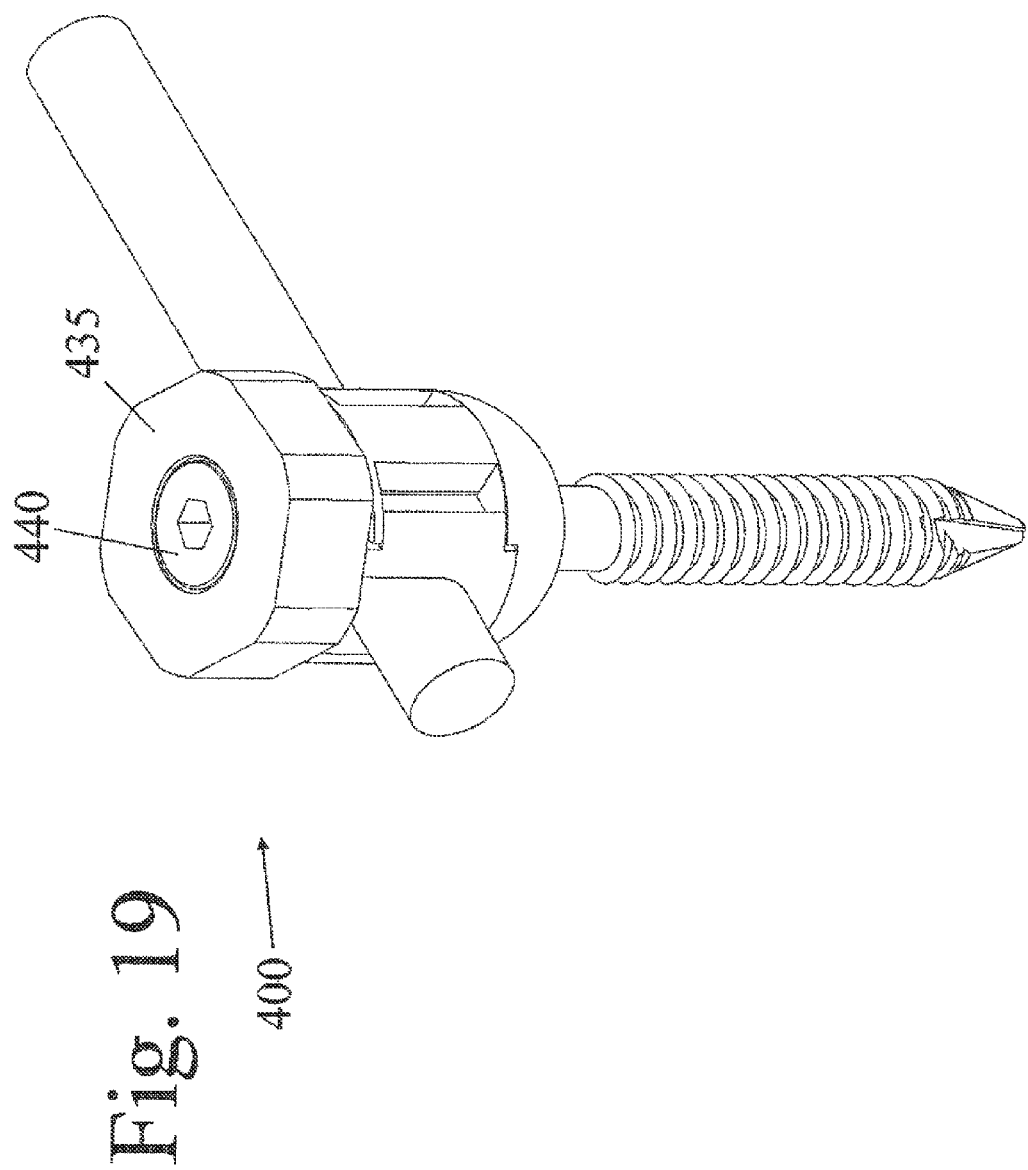
FIG. 19 shows the assembly with the central locking nut engaged within an outer locking nut and the assembly fully assembled.

When complete immobilization is desired, the central locking nut 440 is advanced into a threaded bore in the outer locking nut 435. The central locking nut 440 presses downward against the upper surfaces 1605 (FIG. 16) of the inner saddle member 410 to force the inner saddle member downward against the outer housing 405. The inner saddle member is thereby immobilized relative to the outer housing. In this way, a fixed screw configuration is produced. FIG. 19 shows the assembly 400 with the central locking nut 440 engaged within the outer locking nut 435 and the assembly fully assembled.

The assembled device or any of its components can be made of any biologically adaptable or compatible materials. Materials considered acceptable for biological implantation are well known and include, but are not limited to, stainless steel, titanium, tantalum, combination metallic alloys, various plastics, resins, ceramics, biologically absorbable materials and the like. Any components may be also coated/made with osteo-conductive (such as demineralized bone matrix, hydroxyapatite, and the like) and/or osteo-inductive (such as Transforming Growth Factor "TGF-B," Platelet-Derived Growth Factor "PDGF," Bone-Morphogenic Protein "BMP," and the like) bio-active materials that promote bone formation. Further, the outer surface of the bone screw 425 may be made with a porous ingrowth surface (such as titanium wire mesh, plasma-sprayed titanium, tantalum, porous CoCr, and the like), provided with a bioactive coating, made using tantalum, and/or helical rosette carbon nanotubes (or other carbon nanotube-based coating) in order to promote bone in-growth or establish a mineralized connection between the bone and the implant, and reduce the likelihood of implant loosening. As discussed above, the assembly or its components can also be entirely or partially made of a shape memory material or other deformable material.

A placement and implantation protocol for the assembly 400 is now described. With the assembly 400 in the partially assembled stated shown in FIGS. 15 and 16, a hex-drive screw driver is used to engage the hex-shaped drive cavity 620 (FIG. 6) within the head 610 of the bone screw 425. The driver transverses the bore 925 (FIG. 9) of the inner saddle member 410 and the bore 810 (FIG. 8A) of the locking member 420 to reach the bone screw 425. The screw 425 is then rotated and anchored into the underlying bone. The shank portion 605 of the screw 425 engages the bone such that the screw 425 is locked to the bone.

When used in the spine, the screw 425 can be placed into the pedicle segment of the vertebra. A screw 425 of a second assembly 400 is placed into a second vertebral body on the same side of midline as the first screw. The inter-connecting rod 415 is seated into the rod channel 910 of each inner saddle member 410 such that the rod 415 connects the two assemblies 400 and the respective screws 425. The inner locking nut 430 is used to engage the threads 915 of the inner saddle member 410, but the inner locking nut 430 is not fully tightened. At this point, the rod 415 remains mobile within each rod channel of the saddle members 410.

The outer locking nut 435 is placed and used to engage the threads on the top region of the outer housing 405. The nut 435 is locked thereby immobilizing the bone screw 425 within the outer housing 405. If vertebral re-alignment is desired, the screws 425 are used to re-position the attached vertebral bodies. Since the inner locking nut 430 is not yet locked, the rod 415 can slide within the channels of the saddle members 410 and the screws 425 are still free to move relative to one another.

Figure 20:
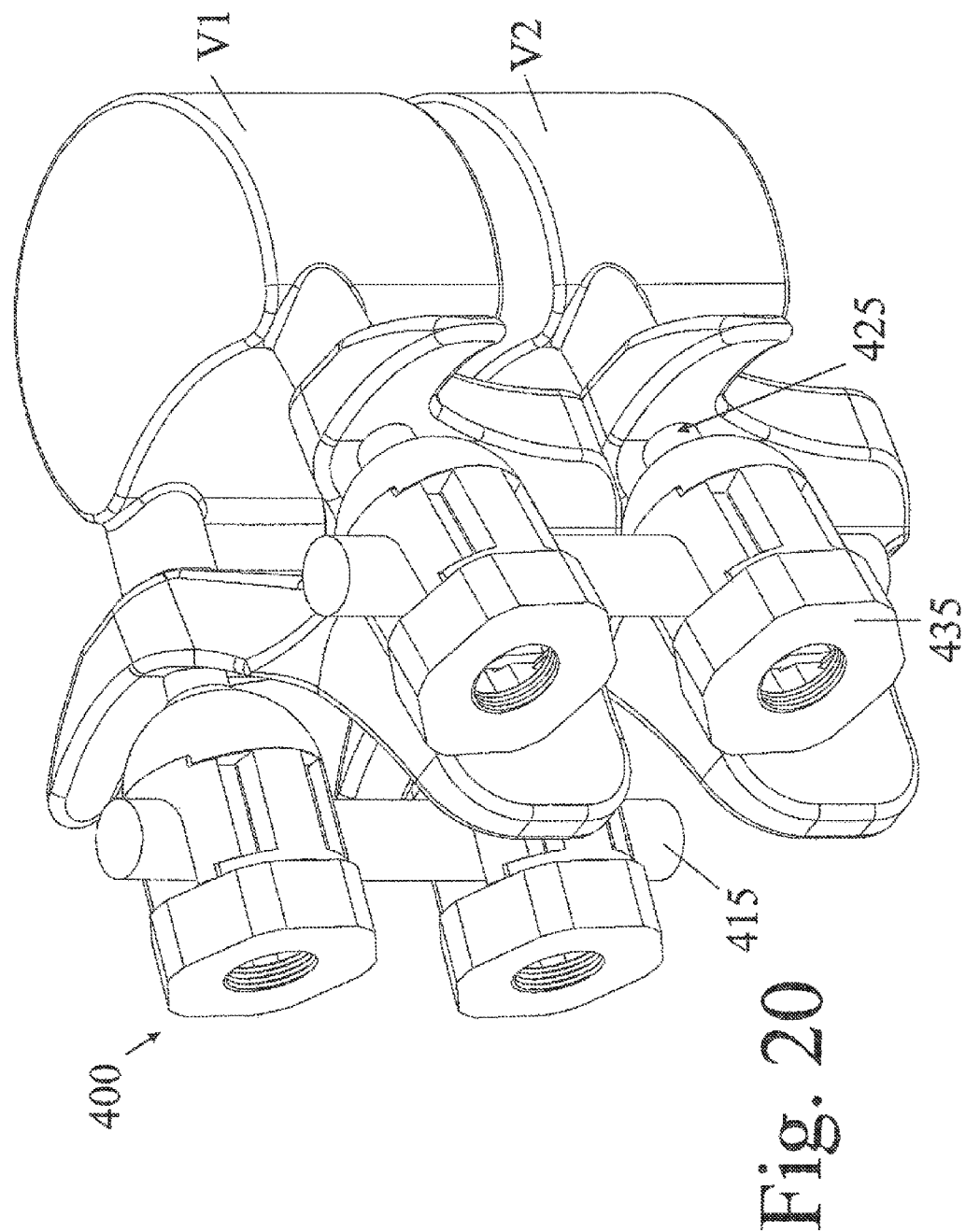
FIGS. 20-22 show vertebral bodies V1 and V2 with a pair of bone screw assemblies attached to each vertebral body.
Figure 22:
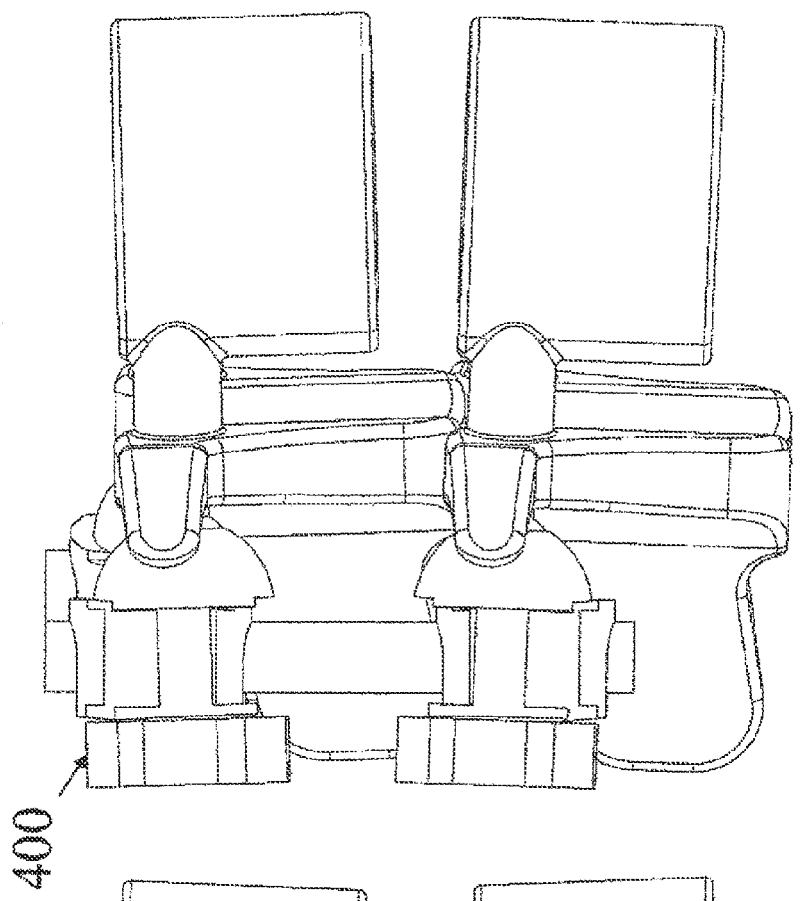
Figure 21:
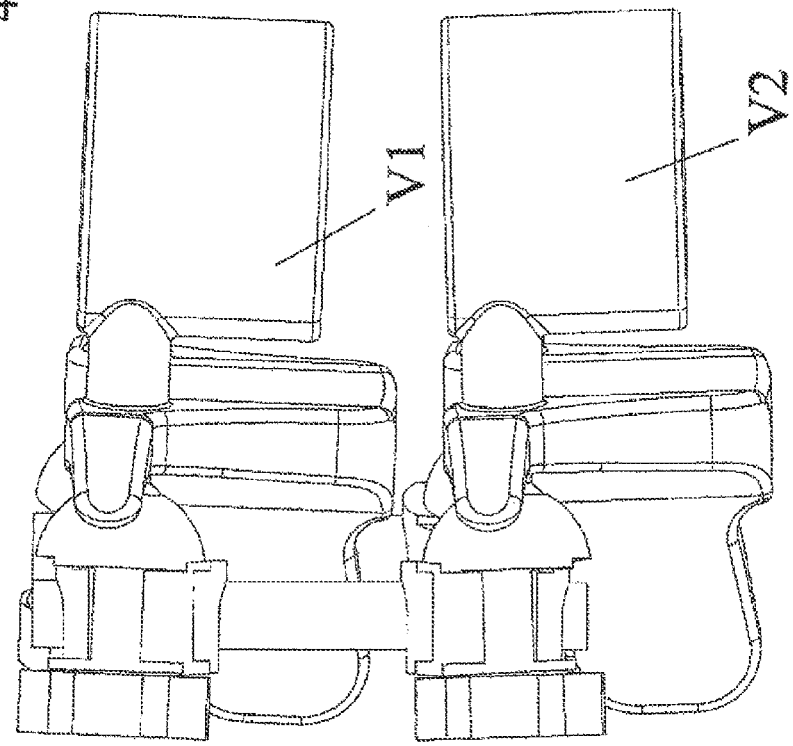

After the screws 425 are appropriately positioned, the inner locking nuts 430 are fully advanced against the rod 415 to lock the rod 415 relative to the inner saddles 415. FIG. 20 shows vertebral bodies V1 and V2 with a pair of assemblies 400 attached to each vertebral body. Two screws 425 can be placed into each vertebral body as shown in FIG. 20. FIGS. 20 and 21 show the vertebral bodies V1 and V2 in flexion and the relative movement permitted by the dynamic screws assemblies 400. Note that each inner saddle member 410 can move within each outer housing 405. FIG. 22 shows the vertebral bodies V1 and V2 in extension. As previously discussed, the spaces 1505 (FIG. 15) may befitted with elastic materials, springs, magnets, or any other device that can resist movement of the saddle member 410 relative to outer housing 405. This feature would enable the screw 425 to return the vertebral bodies to the neutral position after movement. Since the saddle member 410 was slightly undersized in width, a limited amount of vertebral rotation is also permitted. Further, before locking the assembly, the surgeon can freely adjust the orientation of the screw relative to housing without influencing the assembly's neutral position or pre-loading the screw and bone construct.

In one embodiment, a rigid bone screw assembly is attached to a first spinal segment or to any bone structure. The rigid bone screw assembly is configured to completely immobilize a rod relative to a first bone screw that is attached to the spinal segment such that the rod is fixedly cantilevered from the bone screw assembly. The rod is then coupled to a dynamic bone screw assembly of the type described herein such that the rod is placed in proximity to a second bone screw of the dynamic bone screw assembly. The dynamic bone screw assembly permits some movement of the rod relative to the second bone screw. The dynamic bone screw assembly can permit up and down and/or rotational movement between the rod and the second bone screw while prohibiting translational movement. Thus, a rod can be coupled to a rigid bone screw assembly and to a dynamic bone screw assembly wherein each bone screw assembly is attached to a respective spinal segment.

Figure 23:
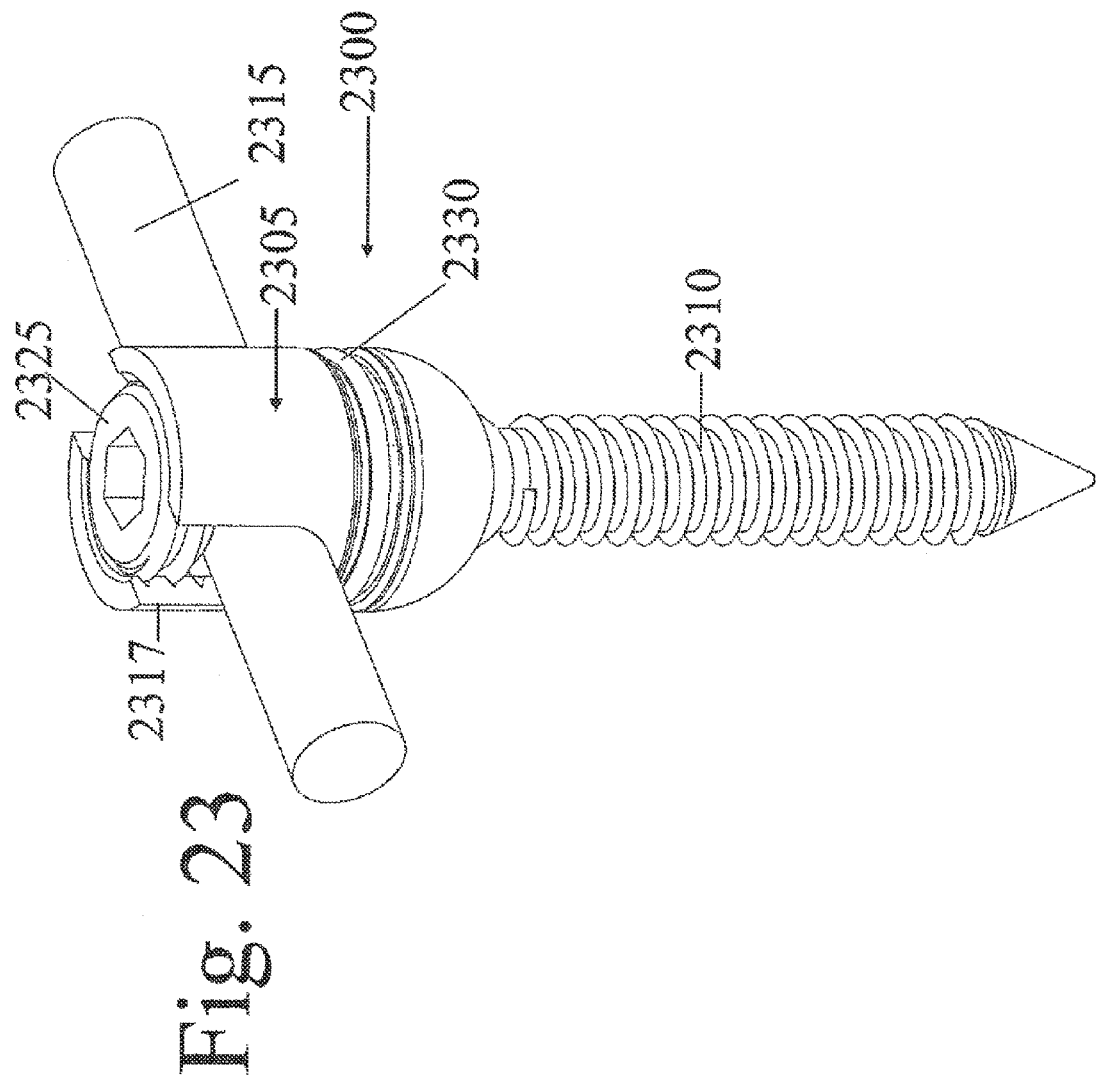
FIG. 23 shows another embodiment of the dynamic bone screw assembly in a fully assembled state.
Figure 24:
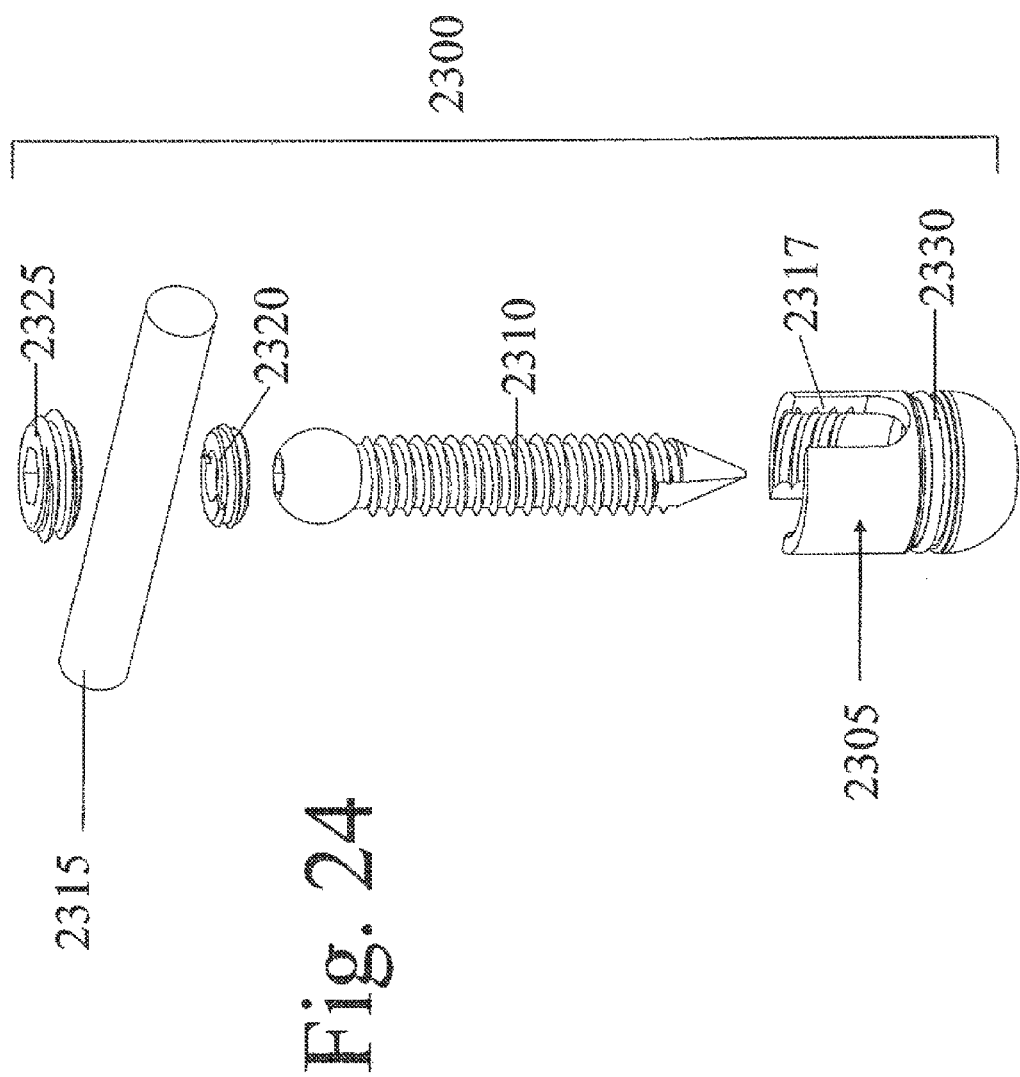
FIG. 24 shows the assembly of FIG. 24 in an exploded state.

FIG. 23 shows another embodiment of the dynamic bone screw assembly in a fully assembled state. FIG. 24 shows the assembly of FIG. 24 in an exploded state. The assembly 2300 includes a housing 2305 that receives a bone screw 2310 through an inner bore in the housing 2305. The housing 2305 includes a slot 2317 that receives a rod 2315. A first locking nut 2320 can be used to lock the bone screw 2310 relative to the housing 2305 by providing a downward force against the head of the bone screw 2310 that immobilizes the bone screw within a seat inside the housing 2305. Likewise, a second locking nut 2325 can be used to lock the rod 2315 relative to the housing 2305 by pressing the rod 2315 downward against a bottom surface of the slot 2317. The housing 2305 includes a flexible or articulating region 2330 that is configured to enable a first region of the housing 2305 to move relative to a second region of the housing 2305, as described below.

Figure 25:
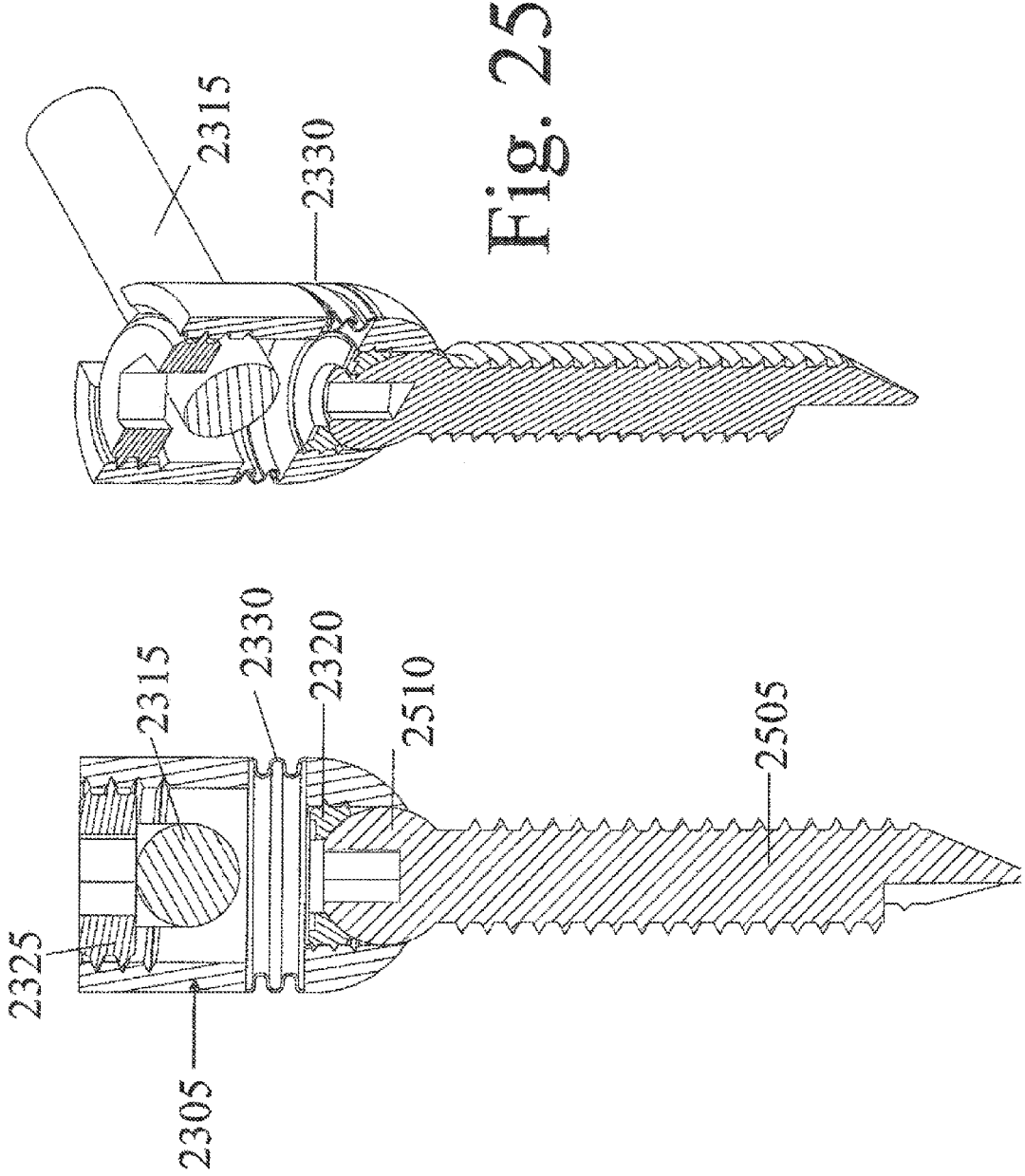
FIG. 25 shows a cross-sectional view of the assembly of FIG. 23.

FIG. 25 shows a cross-sectional view of the assembly of FIG. 23. The screw 2310 has a shank 2505 that extends from a head 2510. The head 2510 sits within a seat formed within the bottom region of the housing 2305. The first locking nut 2320 has threads that engage corresponding threads inside the housing 2305. The first locking nut 2320 can be advanced downward to exert a force on the head 2510 of the screw 2310 to thereby immobilize or lock the screw 2310 relative to the housing 2305. The screw head and/or the seat in which it sits may be serrated, textured, coated, corrugated or otherwise treated in any manner intended to increase the frictional forces between them so as to potentate the locking mechanism. This feature may be equally applied to any other embodiment disclosed in this application.

The rod 2315 sits within the channel 2317 in the housing 2305. The second locking nut 2325 engages a threaded region in the housing 2305 and can be advanced downward against the rod 2215. The second locking nut 2325 provides a downward force to press the rod 2315 against the bottom of the channel 2317 and immobilize the rod 2315 relative to the housing 2305.

As mentioned, the region 2330 of the housing is configured to enable a first region of the housing 2305 to move relative to a second region of the housing 2305. The region 2330 enables the region of the housing that is locked to the rod 2315 to move relative to the region of the housing that is locked to the screw 2310. In this manner, the region 2330 permits the rod 2315 to move relative to the screw 2310 while both the rod and screw are immobilized relative to the housing 2305.

The region 2330 can be configured in various manners so as to permit such movement. In the illustrated embodiment, the region 2330 has a pleated or corrugated configuration that permits the region 2330 to elastically flex or deform such that the segment of the housing 2305 above the region 2330 can move relative to the segment below the region 2330. It should be appreciated that the region 2330 can be configured in various manners so as to permit such movement. Moreover, the region 2330 can be configured to resist movement and to return to a default orientation after a load that caused the movement has dissipated.

Figure 26:
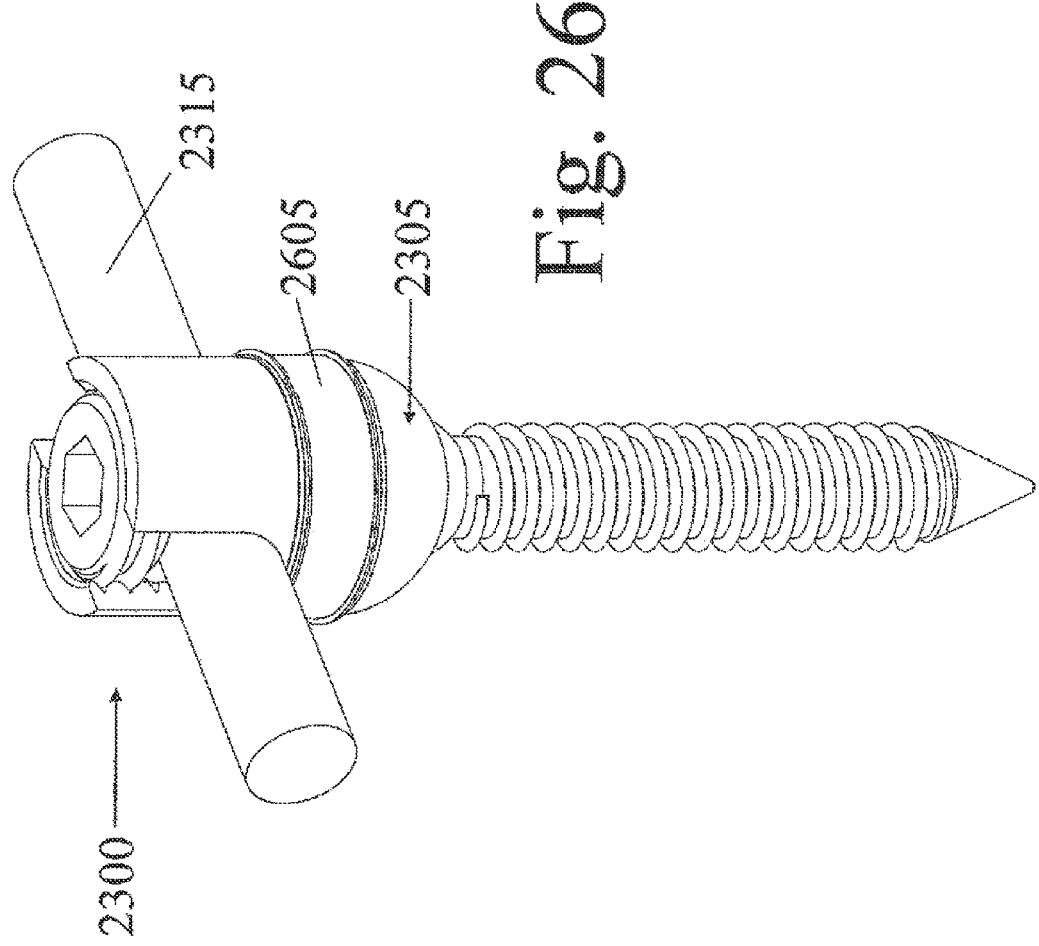
FIG. 26 shows another embodiment of a bone screw assembly.

FIG. 26 shows another embodiment of the assembly wherein the articulating region 2330 is surrounded or covered by a sleeve 2605. FIG. 27 shows a cross-sectional view of the assembly of FIG. 26. The sleeve 2605 is an annular device that fits around the perimeter of the housing 2305 so as to cover the region 2330. The sleeve 2605 can be a membrane that forms a sealed space that prevents migration of any wear debris that may develop. The sleeve 2605 also serves as a barrier against the intrusion of connective tissue and the sealed space may contain a lubricant to reduce friction. A pair of attachment rings 2610 can be used to secure the sleeve 2605 to the housing 2305. While not explicitly illustrated on the other embodiments, this modification can be equally adapted to them. Further, it should be appreciated that before locking the assembly, the surgeon can freely adjust the orientation of the screw relative to housing without influencing the assembly's neutral position or pre-loading the screw and bone construct.

Figure 28:
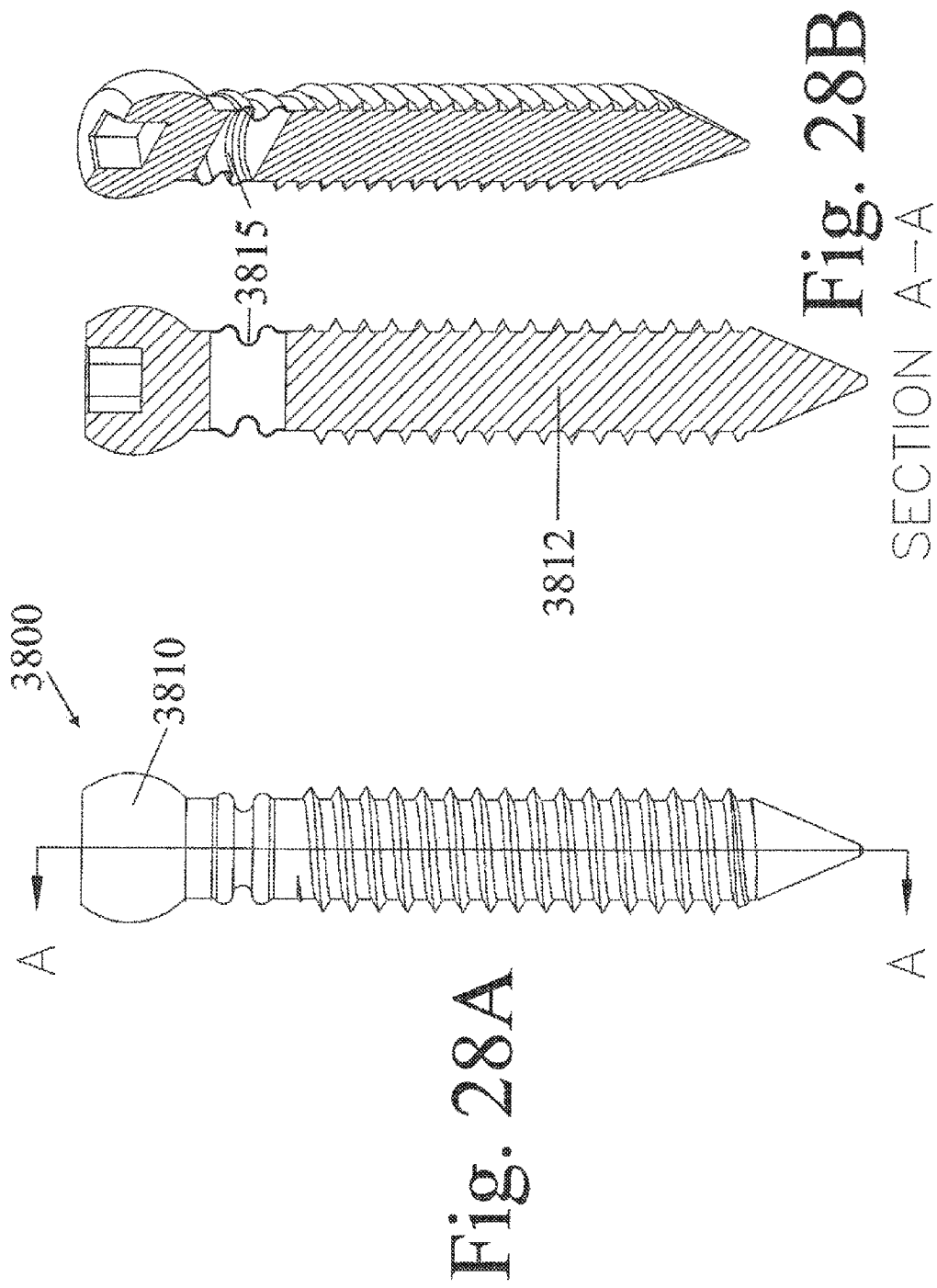
FIGS. 28A-28B show side and cross-sectional views of an additional embodiment of a bone screw

FIGS. 28A-28B show side and cross-sectional views of an additional embodiment of a bone screw 3800. The bone screw 3800 includes a head 3810 and a shank 3812 that extends from the head. The screw 3800 includes contains a movable intermediate segment 3815 between the screw shank 3812 that engages the bone and the screw head 3810 that lies within the housing of a screw assembly. While the remainder of the assembly is not depicted, the remainder can be substantially equal to the housing/rod assembly shown in FIGS. 1 & 2. Alternatively, any screw assembly design that utilizes a rod and bone screw feature may be used. These devices are quite numerous and current art illustrates many variations of these assemblies.

The segment 3815 is configured to enable a first region of the screw 3800 (such as the head 3810) to move relative to a second region of the screw 2800 (such as the shank 3812). The segment 3815 enables the region of the screw that is that is locked to the housing and rod to move relative to the region of the housing that is locked to bone. In this manner, the segment 3815 permits the rod to move relative to the screw while both the rod is immobilized relative to the housing.

The segment 3815 can be configured in various manners so as to permit such movement. In the illustrated embodiment, the segment 3815 has a pleated or corrugated configuration that permits the segment 3815 to elastically flex or deform such that the head 3810 above the segment 3815 can move relative to the shank 3812 below the segment 3815. It should be appreciated that the segment 3816 can be configured in various manners so as to permit such movement. In this device, a dynamic screw assembly is created by providing movement within the bone screw itself. As in the embodiment shown in FIGS. 26 and 27, a flexible sleeve or membrane may be used to surround the segment 3815 of movable articulation.

Figure 29:
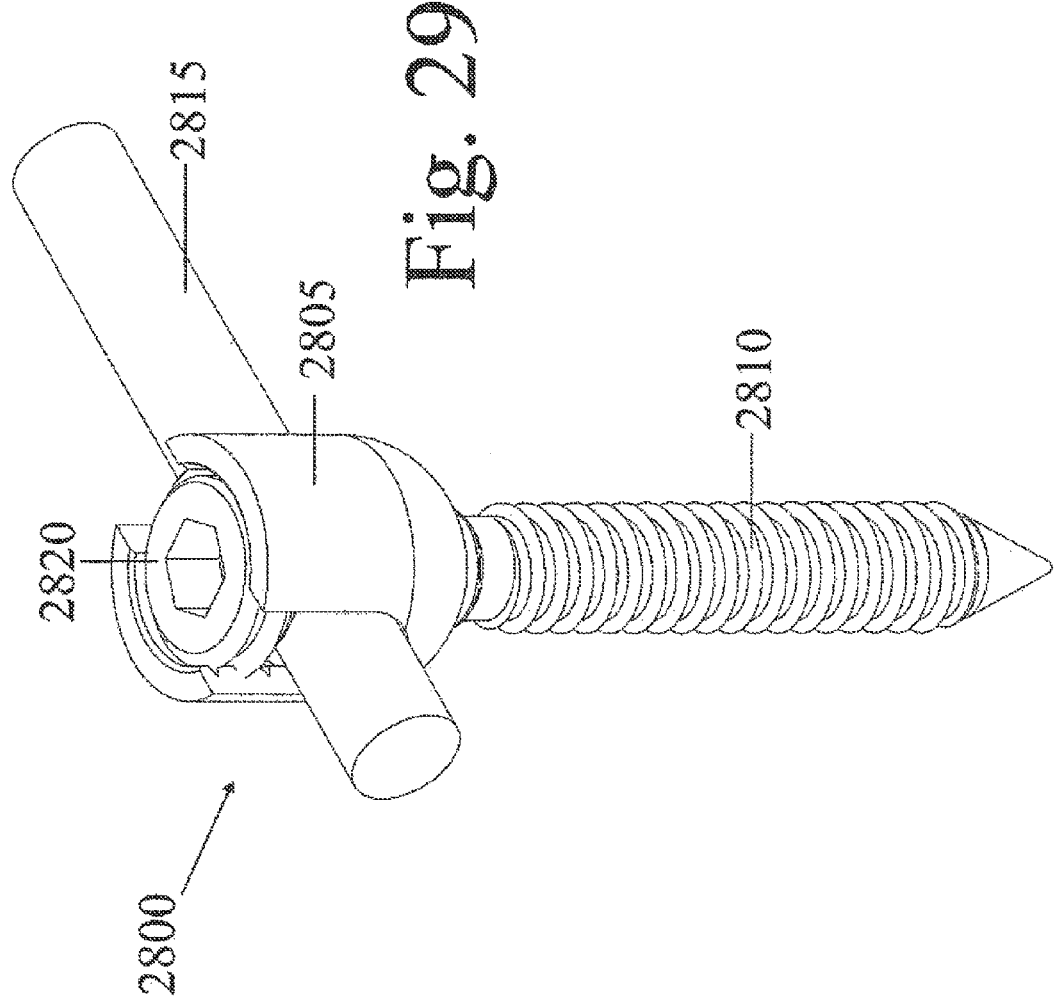
FIG. 29 shows yet another embodiment of a bone screw assembly.
Figure 30:
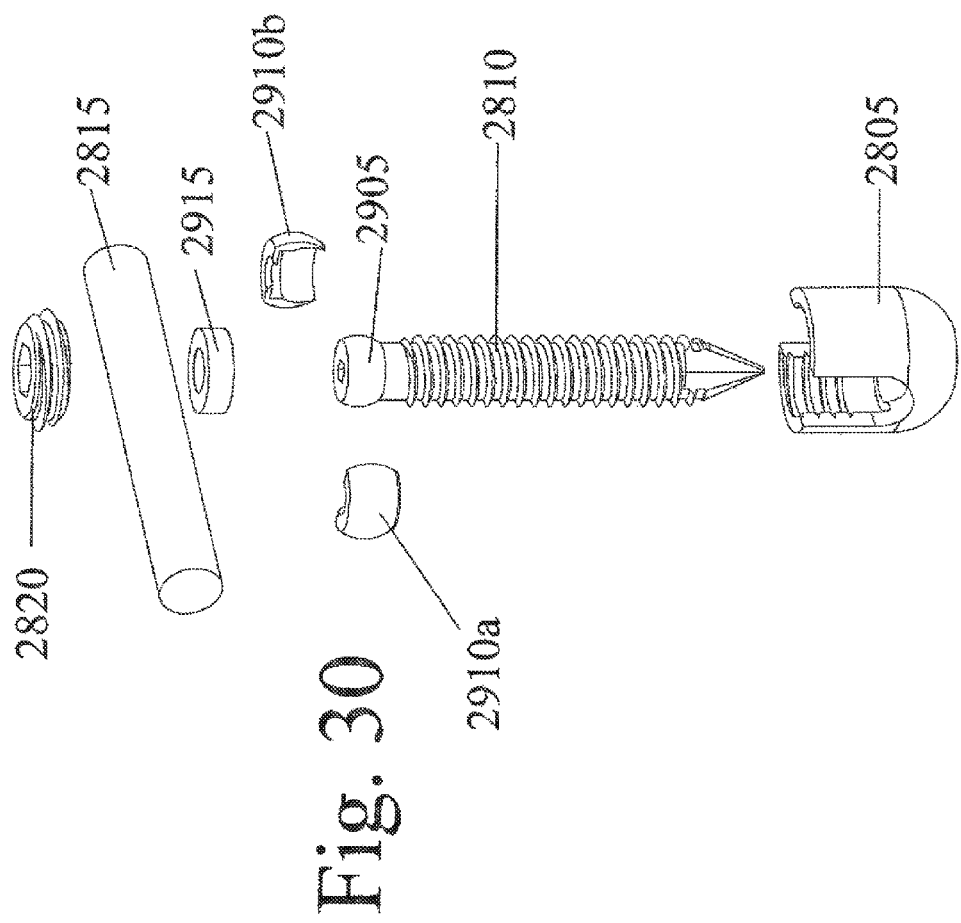
FIG. 30 shows an exploded view of the assembly of FIG. 28.

FIG. 29 shows yet another embodiment of the dynamic bone screw assembly. FIG. 30 shows an exploded view of the assembly of FIG. 29. In this embodiment, the head of the screw is positioned within an inner housing member in which the head can rotate in a ball and socket manner. The inner housing member can be immobilized relative to the housing to fixedly attach the screw to the housing. However, the head of the screw can rotate within the inner housing member to permit some movement between the screw and the housing. In addition, the head can be completely immobilized within the inner housing.

With reference to FIGS. 29 and 30, the bone screw assembly 2800 includes an outer housing 2805, a bone screw 2810, and a rod 2815. A locking nut 2820 can be threaded into the housing 2805 to provide a downward force onto the rod 2815 and immobilize the rod relative to the housing 2805 and the inner housing (2910a & b). As best shown in FIG. 30, the bone screw 2810 has a head 2905 that can be positioned within inner housing members 2910a and 2910b. While not shown, half members 2910a & b are joined to form the assembled inner housing member using threaded screws, ratchets, clips, adhesives, or any other technique for segment assembly. A saddle 2915 is positioned within the housing 2805 below the rod 2815 and above the inner housing members 2910 in the assembled device.

Figure 31:
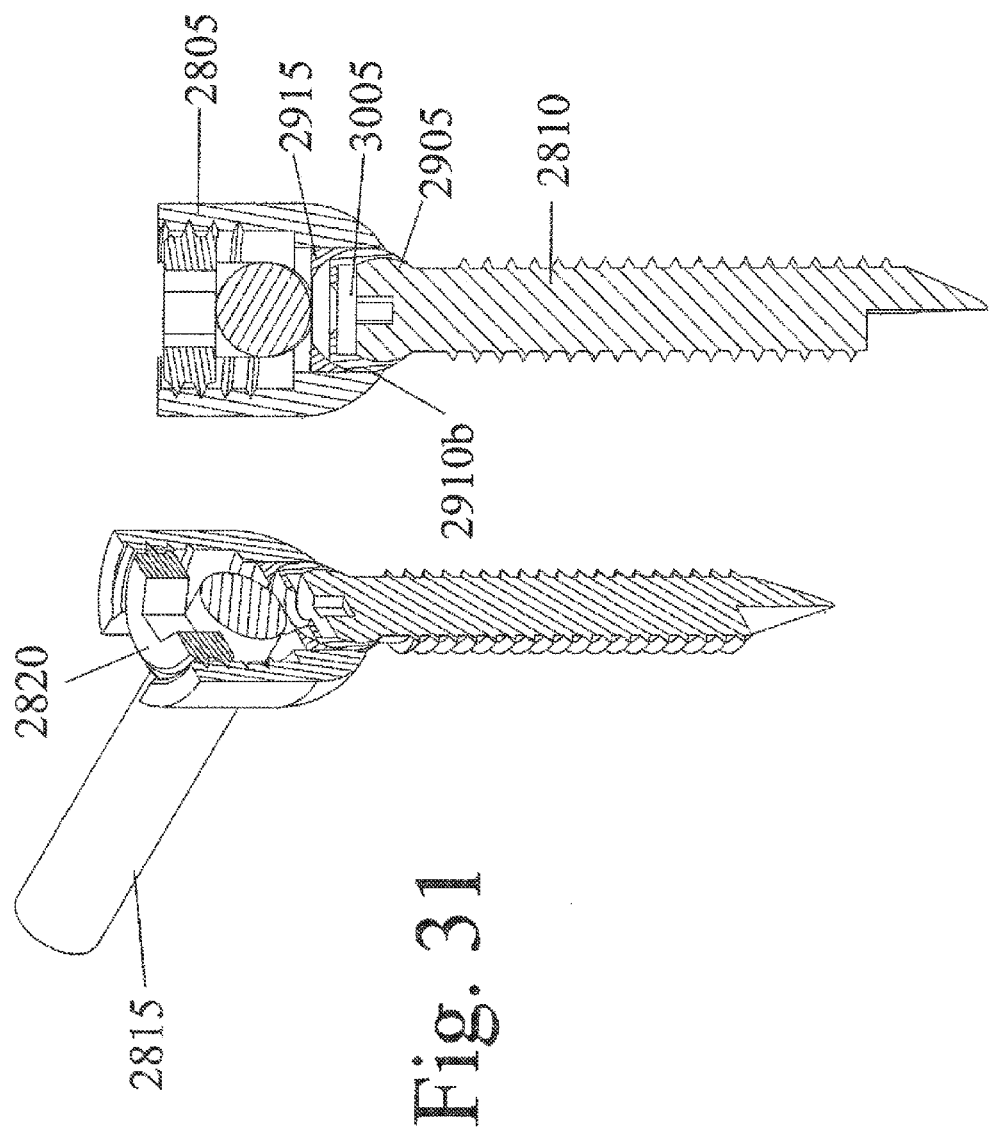
FIG. 31 shows a cross-sectional view of the assembly of FIG. 28.

FIG. 31 shows a cross-sectional view of the assembly of FIG. 29. The head 2905 of the screw 2910 is positioned within the inner housing members 2910, which collectively form a socket for the head 2905. The socket contains a space 3005 that is positioned, for example, above the head 2905. The saddle 2915 is positioned directly above the inner housing 2910 assembly and below the rod 2815.

The locking nut 2820 is advanced toward the rod 2815 to tightly press the rod 2815 against the upper edge of the saddle 2915. This also causes the saddle 2915 to press downward against the inner housing members 2910 and force the inner housing members 2910 against a seat in the housing 2805, which causes rigid immobilization of the rod 2815, housing 2805, and inner housing members 2910 relative to one another. However, the head 2905 of the bone screw 2810 is movable within the inner aspect of the inner housing members 2910 to produce the dynamic aspect of the assembly. That is, the head 2905 of the screw 2810 can rotatably move within the socket formed by the inner housing members 2910.

The space 3005 within the inner housing member 2910 can contain a material or structure that resists movement of the head 2905 of the bone screw 2810 relative to the inner aspect of the inner housing members 210. The material or structure within the space 3005 can be, for example, an elastic material(s), fluids, spring device(s), magnets or any other appropriate materials/devices that will resist movement of the head of bone screw relative to the inner aspect of the inner housing members. When the screw head is moved out of a predetermined position in the inner housing members, the material/device within space 3005 will apply a force to the head of screw and resist any bone screw movement away from the neutral position. With movement, the assembly would return the screw and the attached bone to the neutral position once the deflecting force has dissipated. Further, before looking the assembly with the looking nut 2820, the surgeon can freely adjust the orientation of the screw relative to housing without influencing the assembly's neutral position or pre-loading the screw and bone construct.

Figure 32:
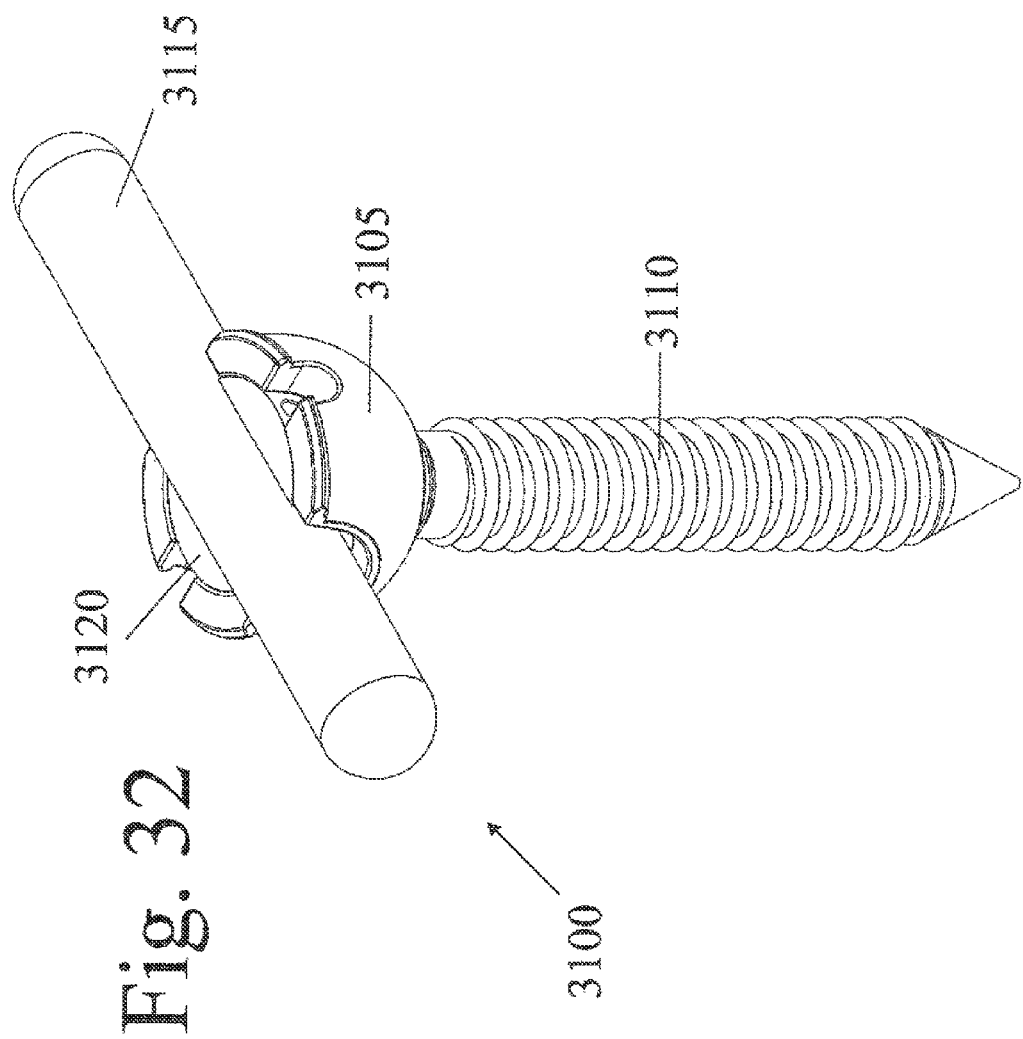
FIG. 32 shows another embodiment of a dynamic bone screw assembly.
Figure 33:
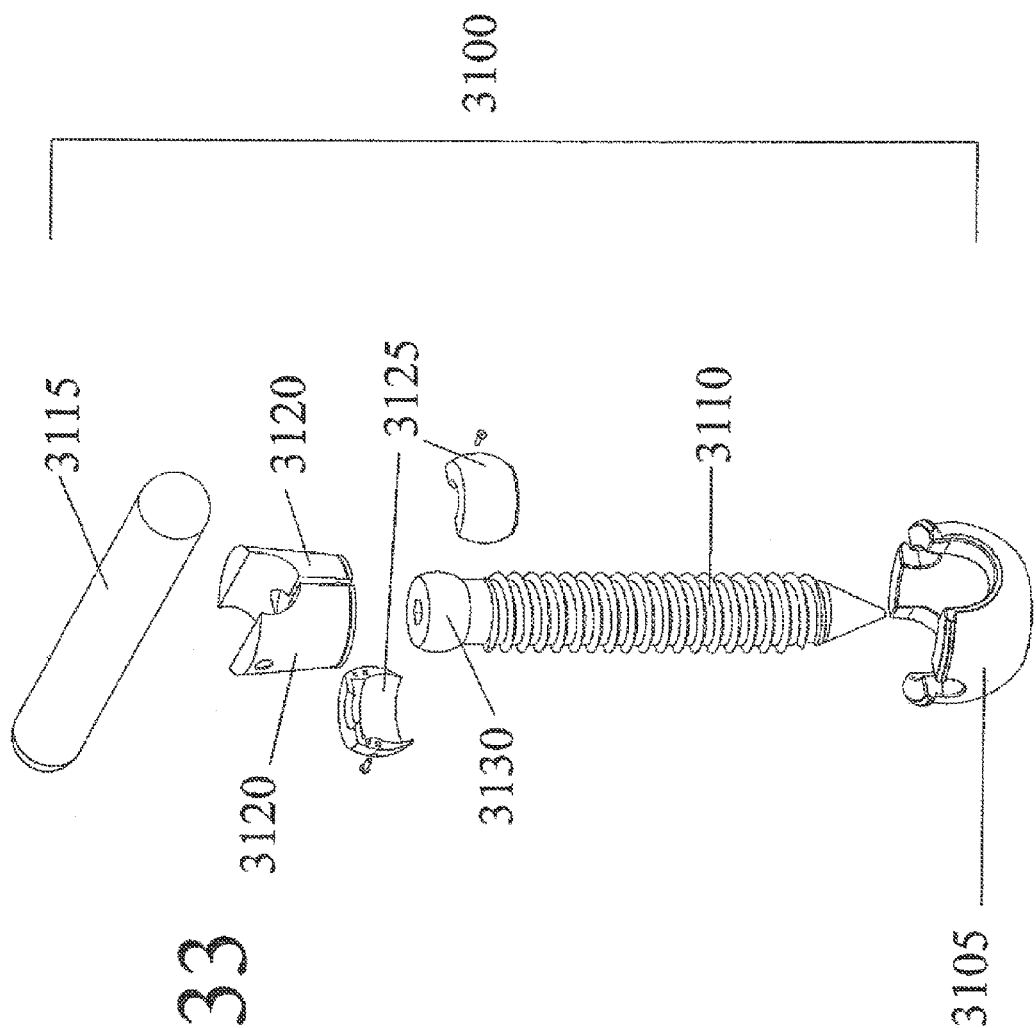
FIG. 33 shows the bone screw assembly of FIG. 32 in an exploded state.

FIG. 32 shows another embodiment of a dynamic bone screw assembly. FIG. 33 shows the bone screw assembly of FIG. 31 in an exploded state. The bone screw assembly 3100 includes a housing 3105, a bone screw 3110 that fits through a bore in the housing 3105, and a rod 3115. The rod 3115 lockingly engages a pair of locking members 3120. A pair of rotational member 3125 (FIG. 33) fit over the head 3130 and within the locking members 3120, as shown in the cross-sectional view of FIG. 34. Thus, when assembled, the rotational members 3125 are interposed between the head 3130 of the screw 3110 and the inner aspect of the looking members 3120. While illustrated as using screws, the rotational members 3130 can be attached to one another in various manners, such as using threaded screws, ratchets, clips, adhesives, or any other technique for segment assembly.

Figure 34:
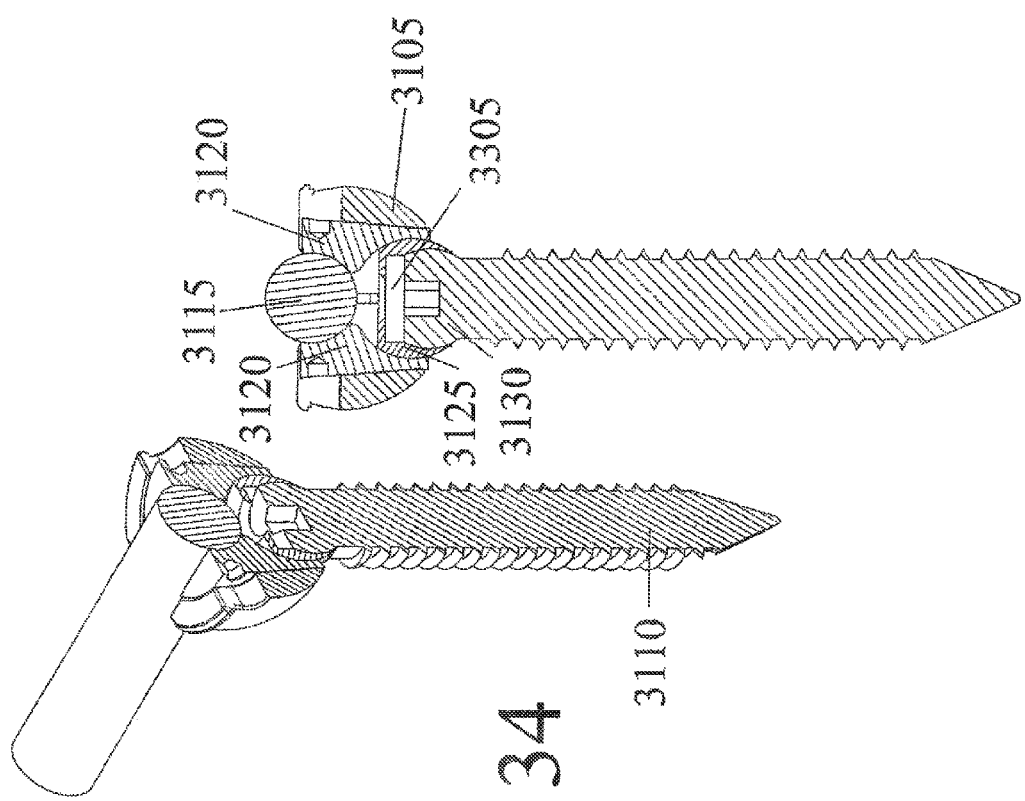
FIG. 34 shows a cross-sectional view of the assembly of FIG. 32.

FIG. 34 shows a cross-sectional view of the assembly of FIG. 32. The locking members 3120 can lock to the housing 3105 the rod 3115 using a Morse taper configuration. When the locking members 3120 are pressed downward into the housing 3105 by the rod 3115, the two locking members 3120 are forced inward toward the rod 3115 to immobilize the rod 3115 therebetween. With the assembly in the locked configuration, the outer surfaces of the locking members 3120 tightly fit within the inner surface of the housing 3105. The individual segments of the locking members 3120 are forced inward and immobilize the rod 3115 and the rotational members 3125 relative to one another. In this way, the assembly serves to lock the rod 3115 relative to the bone screw 3110.

Although a Morse taper locking mechanism provides a powerful immobilization, it may be loosened with only a modest backout of the locking members 3120 relative to the housing 3105. This may be prevented by the addition of a ratchet locker, wedge locker, protrusion/indentation locker, or any other locking mechanism to prevent backout and/or loosening of the Morse taper.

With reference to the cross-sectional view of FIG. 34, a space 3305 is located between an upper surface of the screw head 3130 and an inner surface of the assembled rotational members 3125. The space 3305 can contain deformable material, spring device(s), magnet(s), or any other material or device that can resist movement of the upper surface of the head 3130 relative to the inner surface of the assembled rotational members 3125. When the assembly is in the unlocked state, the screw 3110 and the rotational members 3125 are freely movable within the locking members 3120.

Figure 35:
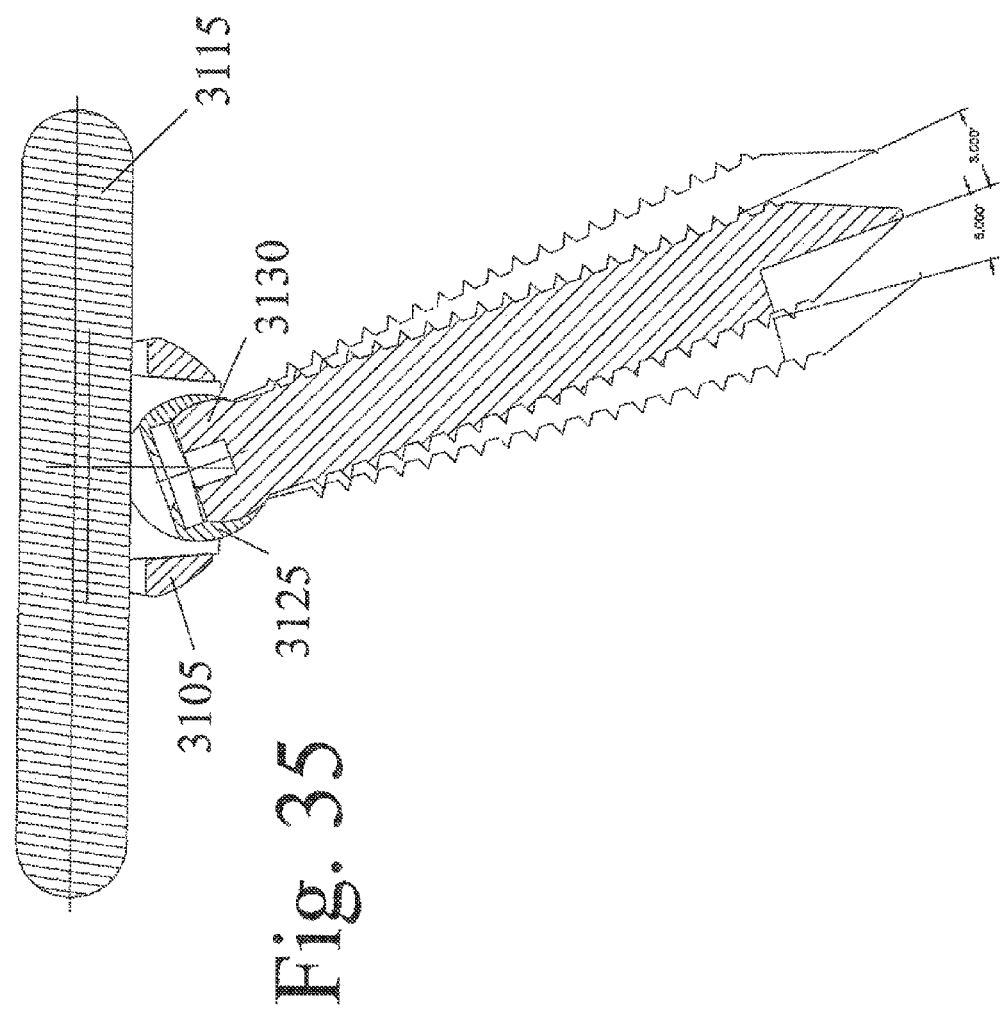
FIG. 35 shows how the screw of the assembly can rotate to various positions.

When the assembly is locked, the rotational members 3125 are immobilized relative to the locking members 3120, but the screw head 3130 can still rotate within the rotational members 3125. The material or device within the space 3305 applies a force to the screw head 3130 and resists movement of the screw head. In this manner, the screw resists a deflecting force but can also move within the rotational members 3120 if the force is of a sufficient magnitude. When the force has dissipated, the screw returns to the neutral position. FIG. 35 shows how the screw 130 can rotate to various positions. Note that before locking the assembly, the surgeon can freely adjust the orientation of the screw relative to housing without influencing the assembly's neutral position or pre-loading the screw and bone construct. If desired, the head of the screw can be completely immobilized within the rotational members 3125.

FIG. 36 shows the screw assembly of FIG. 32 placed into the pedicle portion of a vertebra. Four screw assemblies 3100 have been placed into the two vertebras V1 and V2. Interconnecting rods 3115 are used to connect the two screw assemblies 3100 on each side of the midline and all of the screw assemblies 3100 are then locked. The screw assemblies permit dynamic fixation of the vertebral bodies.

Figure 37A:
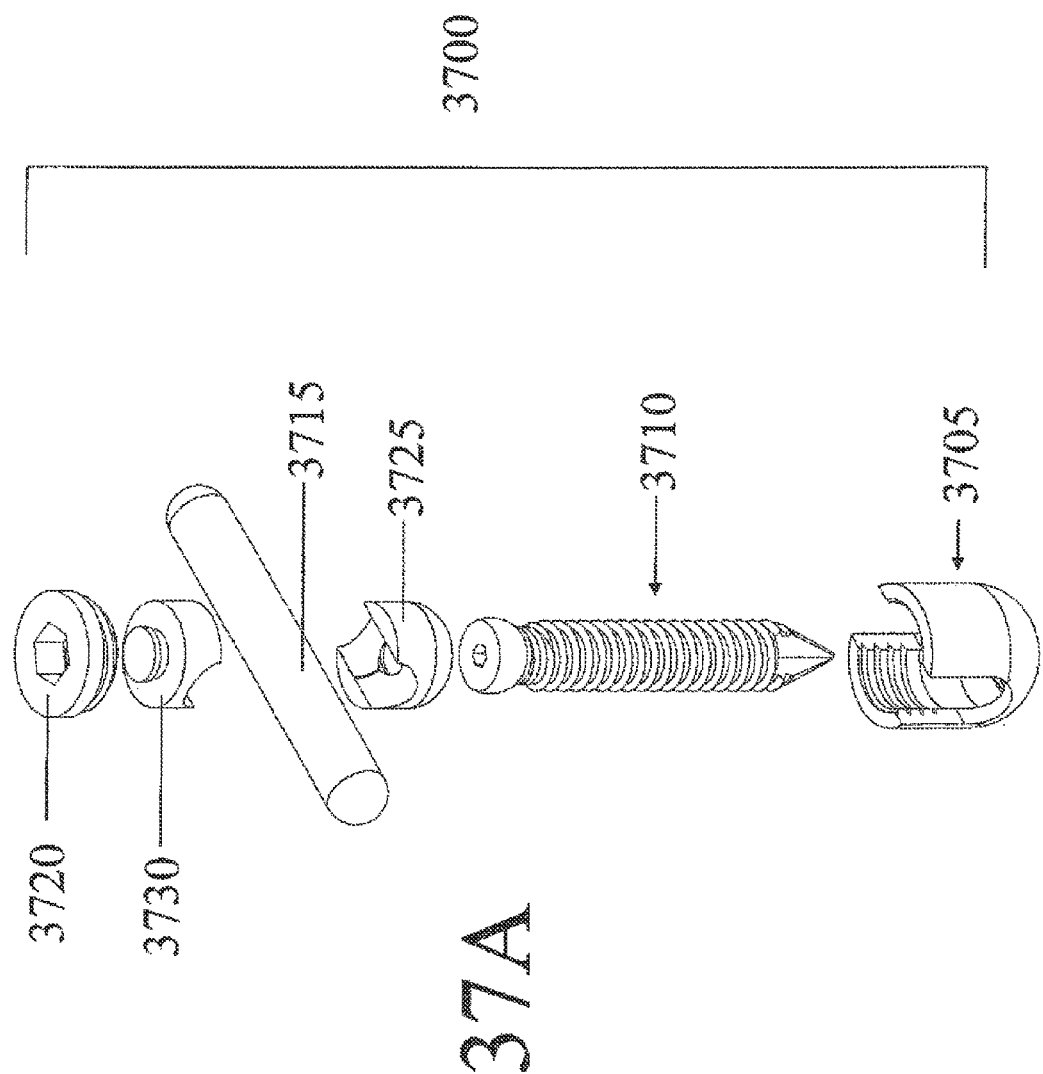
FIG. 37A shows an exploded view of another embodiment of a dynamic bone screw assembly.
Figure 37B:
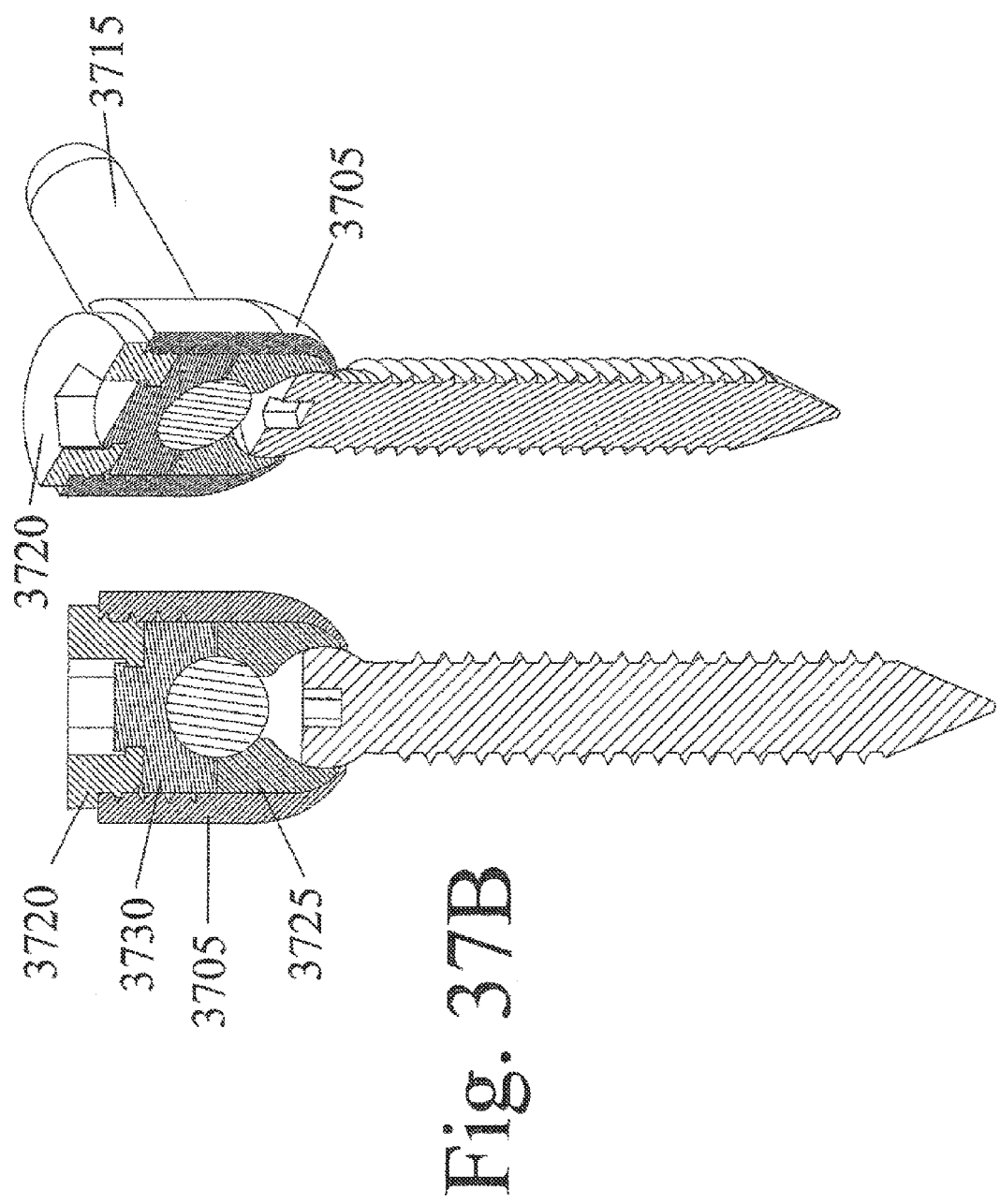
FIG. 37B shows a cross-sectional view of the bone screw assembly of FIG. 37A.
Figure 37C:
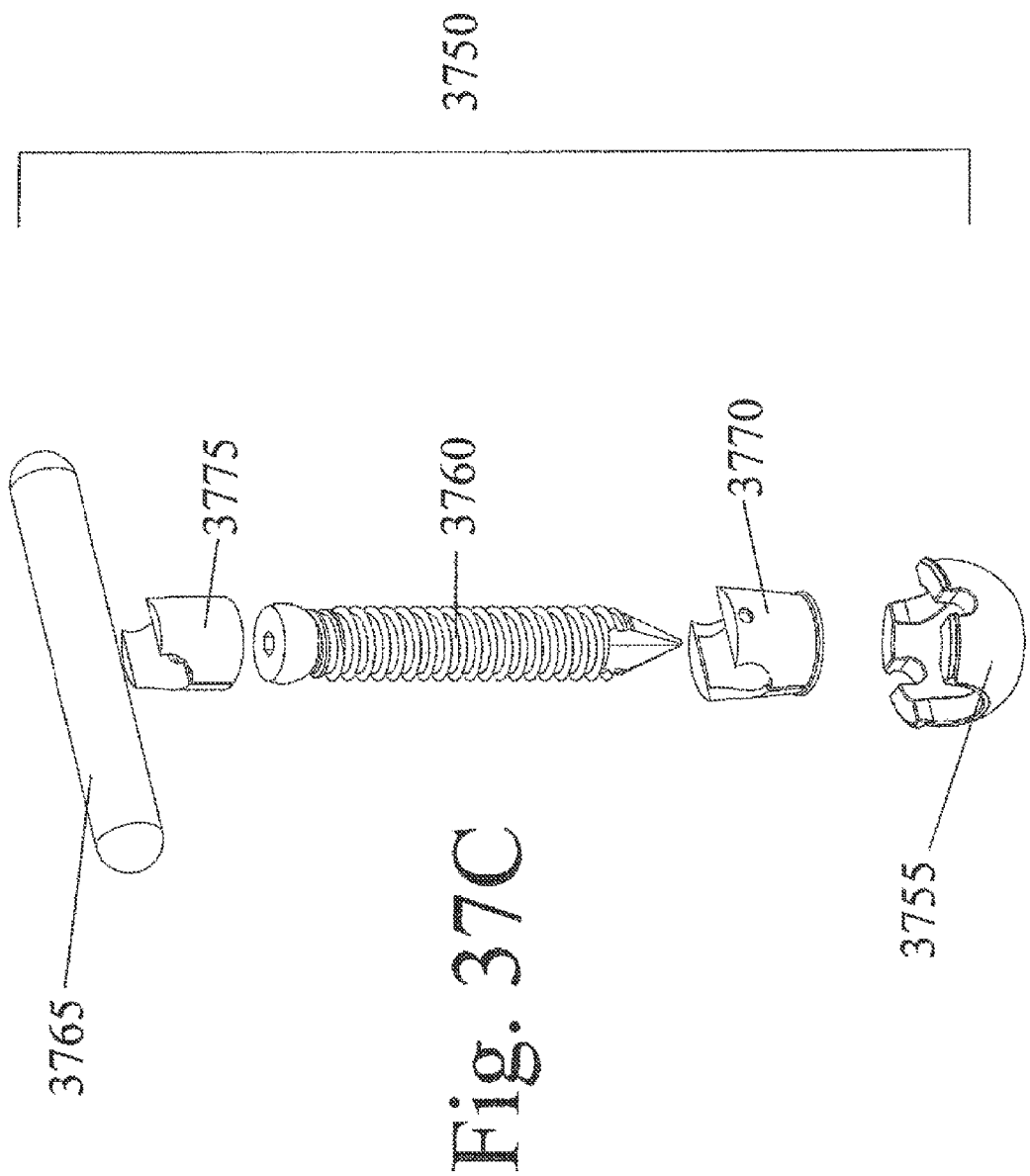
FIG. 37C shows an exploded view of another embodiment of a dynamic bone screw assembly.

FIGS. 37A-C show additional embodiments of bone screw assemblies wherein a rod can be immobilized using a Morse taper assembly, such as was described above. One or more of the components of the assembly can be manufactured of a deformable material that permits some relative movement between the screw and the rod when a force of sufficient magnitude is applied thereto. In this manner, a dynamic screw assembly can be achieved.

FIG. 37A shows an exploded view of an embodiment of a dynamic bone screw assembly 3700. FIG. 37B shows a cross-sectional view of the bone screw assembly of FIG. 37A. The bone screw assembly 3700 includes a housing 3705, a bone screw 3710, a rod 3715, a locking nut 3720, and an inner housing 3725. An upper member 3730 is positioned above the rod 3715 and is rotatably attached to an underside of the locking nut 3720. As shown in the cross-sectional view of FIG. 37C, the rod 3715 is compressed between the inner housing 3725 and the upper member 3730 when the locking nut 3720 is advanced downward into the housing 3705. The housing 3705 has a bore that is large enough to receive a shank portion of the screw 3710, but not large enough that the head of the screw 3710 can pass through the bore.

The upper member 3730 and the inner housing 3725 can be manufactured of a deformable material or a shape-memory memory material to permit the screw 3710 to be rotated out of the neutral position. The material is deformed when the screw 3710 is moved out of the neutral position, but provides a force on the screw the urges the screw back towards the neutral position.

Figure 37D:
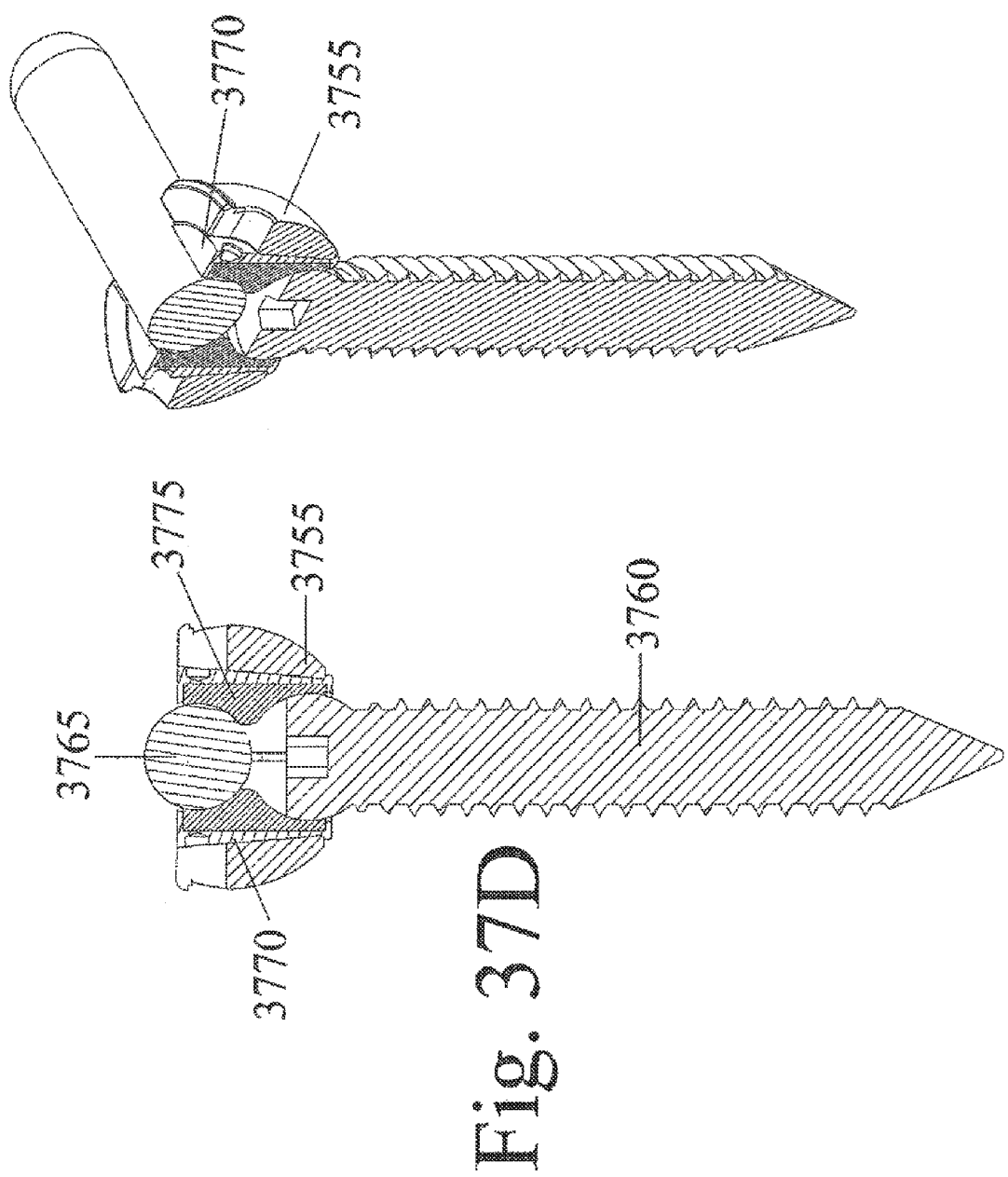
FIG. 37D shows a cross-sectional view of the bone screw assembly of FIG. 37C.

FIG. 37C shows an exploded view of another embodiment of a dynamic bone screw assembly 3750. FIG. 37D shows a cross-sectional view of the bone screw assembly of FIG. 37C. The bone screw assembly 3750 includes a housing 3755, a bone screw 3760, a rod 3765. The housing includes an inner sleeve 3770 that surrounds a deformable inner housing 3775. The rod 3765 can be advanced downward to clamp the rod and 3765 and the head of the screw 3760 within the inner housing 3775 using a Morse type configuration. The inner housing 3775 can be manufactured of a deformable material or a shape-memory memory material to permit the screw 3760 to be rotated out of the neutral position. The material is deformed when the screw 3760 is moved out of the neutral position, but provides a force on the screw the urges the screw back towards the neutral position.

The dynamic bone screw assemblies of the type described herein provide one or more movable elements between the screw shaft and the rod. In this way, the rod can be immobilized relative to one movable element while the second movable element provides continued movement of the screw shaft relative to the rod. Regardless of the particular locking mechanism, such a feature can be used to provide dynamic stabilization of the bony elements.

Figure 38:
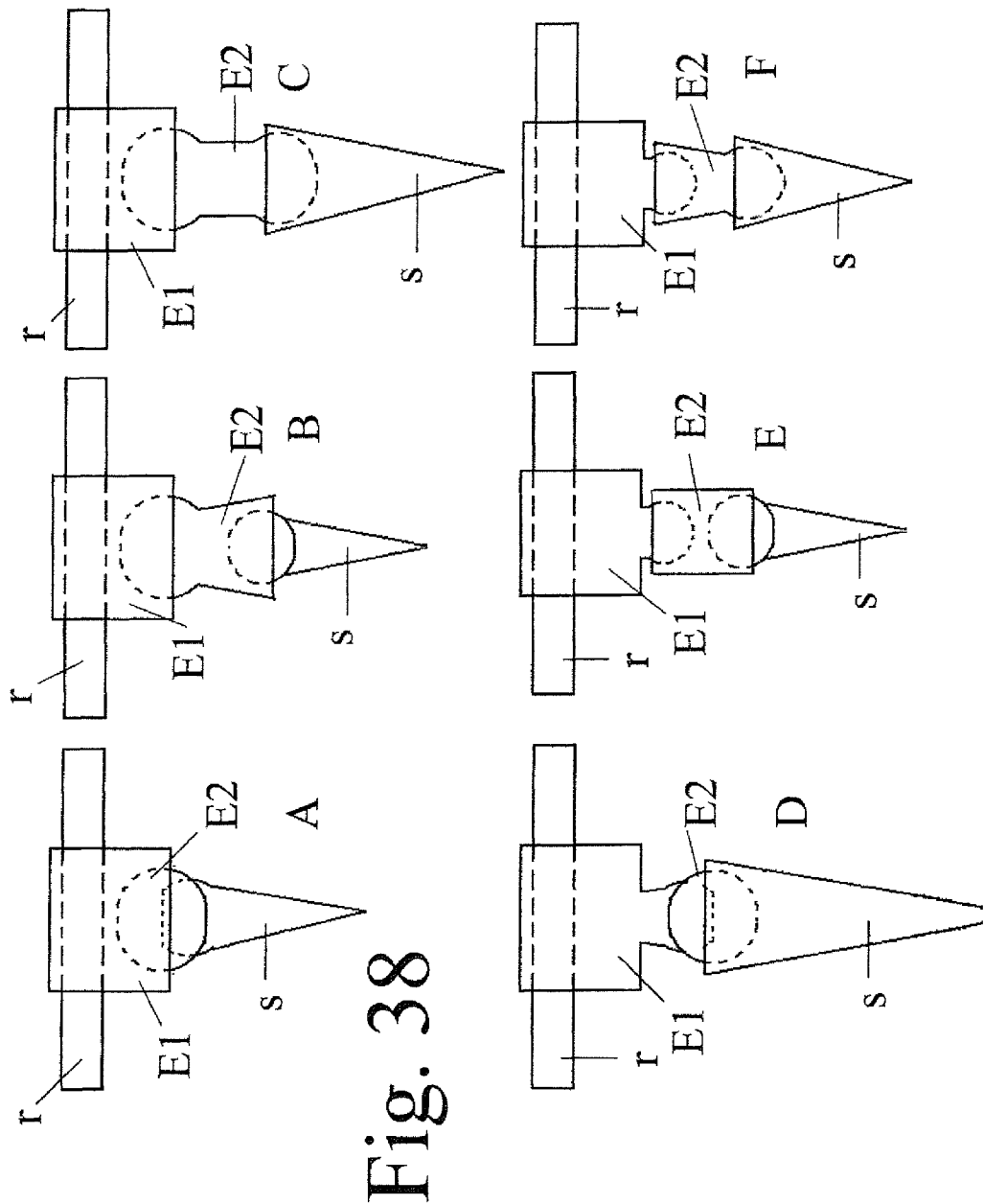
FIG. 38 show various schematic embodiments of bone screw assemblies that employ multiple moving surfaces or elements.

FIG. 38 show various schematic embodiments of bone screw assemblies that employ multiple moving surfaces or elements. A generic locking mechanism is shown in conjunction with a rod R, a bone screw S and two elements E1 and E2 that can move relative to one another. The rod R can be locked or immobilized relative to element E1, while the screw S can be locked or immobilized relative to element E2. In embodiments A, B and C, the element E2 is movably disposed within element E1 and in embodiments C, D, and E, the element E1 is movably disposed within element E2. In embodiment B, the element E2 extends downwardly from element E1 to displace the screw S from element E1. Embodiment C also displaces the screw S, but the element E2 has a portion that is positioned inside the screw S. In embodiment D, the element E1 is disposed within element E2, and element E2 is disposed within the screw S. In embodiment E, the element E1 and the screw are both disposed within the element E2. Finally, in embodiment F, the element E1 is disposed within element E2, which is disposed within the screw S. One of ordinary skill in the art can add additional surfaces or elements to achieve further embodiments of this invention and it is understood that these would fall within the scope of this application.

Although embodiments of various methods and devices are described herein in detail with reference to certain versions, it should be appreciated that other versions, embodiments, methods of use, and combinations thereof are also possible. Further, the design elements and modifications disclosed in the application that permit dynamic movement between rod and bone screw may be alternatively applied to any screw assembly that utilizes a rod and bone screw feature. These devices are quite numerous and current art illustrates many variations of these assemblies that are presently configured for rigid fixation alone. (e.g., U.S. Pat. Nos. 5,810,819; 6,139,549; 6,371,957; 6,379,357; 6,478,798; 6,565,565; 6,610,063 and many others disclose variations of these devices.) Therefore the spirit and scope of the appended claims should not be limited to the description of the embodiments contained herein.

What is claimed is:

1. A bone fixation assembly, comprising:
   an interconnecting member;
   a bone fastener comprising a head segment and a shank configured to extend therefrom, said head segment configured to couple to a first segment of a driver, said driver configured to advance said bone fastener onto a bone;
   a first housing comprising:
      a top surface, an opposing bottom surface, and at least one interconnecting side surface;
      a first internal bore configured to extend from said top surface to said bottom surface along a first axis; and
      at least a seat configured to receive at least a portion of said head segment of said bone fastener;
   a second housing comprising:
      a top surface, an opposing bottom surface, and at least two opposing side surfaces configured to connect said top and bottom surfaces;
      a first bore configured to extend from a first one of said side surfaces to an opposing one of said side surfaces, said first bore sized to seat said interconnecting member; and
      a second bore configured to extend from said top surface to said bottom surface along a second axis, said second bore sized to permit advancement of said first segment of said driver therethrough; and
   a locking feature configured to transition from a first state to a second state, said first state configured to enable said second housing to be movable relative to said first housing along a trajectory that is non-parallel to said first axis of said first housing, and said second state configured to rigidly affix said first housing relative to said second housing; and
   wherein said first housing and said second housing are configured to movably couple and to attain a range of positions relative to one another, at least one of said positions comprising said first axis of said first housing being coaxially aligned with said second axis of said second housing.

2. The bone fixation assembly of claim 1, wherein said second housing comprises a locking feature configured to transition from a first state to a second state, said first state configured to enable said second housing to be movable relative to said interconnecting member, and said second state configured to rigidly immobilize said second housing relative to said interconnecting member.

3. The bone fixation assembly of claim 1, wherein said first housing comprises a locking feature configured to transition from a first state to a second state, said first state configured to enable said first housing to be movable relative to said head segment of said bone fastener, and said second state configured to rigidly immobilize said first housing relative to said head portion of said bone fastener.

4. The bone fixation assembly of claim 1, wherein said first and said second housing are configured to cooperatively interact between an extension of one of said first or second housing and a cavity of the other of said first or second housing.

5. The bone fixation assembly of claim 4, wherein said range of positions attainable by said first and said second housing is limited by said cooperative interaction between said first and said second housing.

6. The bone fixation assembly of claim 1, wherein said first housing is configured to move relative to said second housing along a trajectory, said trajectory comprising a pathway which is non-parallel to said second axis of said second housing.

7. A bone fixation assembly, comprising:
an interconnecting member;
a bone fastener comprising a head segment and a shank configured to extend therefrom, said head segment configured to couple to a first segment of a driver, said driver configured to advance said bone fastener onto a bone;
a first housing comprising:
opposing top and bottom surfaces;
a first internal bore configured to extend from said top surface to said bottom surface along a first axis; and
a seat configured to receive at least a portion of said head segment of said bone fastener; and
a second housing comprising:
opposing top and bottom surfaces;
opposing first and second side surfaces;
a first bore configured to extend from said first side surface to said second side surface, said first bore sized to seat said interconnecting member; and
a second bore configured to extend from said top surface to said bottom surface along a second axis, said second bore sized to permit said first segment of said driver therethrough; and
a locking feature configured to transition from a first state to a second state, said first state configured to enable said first housing to move relative to said bone fastener, and said second state configured to cause said first housing to be immovably positioned relative to said bone fastener;
wherein said second housing configured to movably couple to said first housing and to move relative to it along a trajectory that is non-parallel to said first axis of said first housing; and
wherein said second housing is configured to attain a range of positions relative to said first housing, at least one of said positions comprising said first axis of said first housing being coaxially aligned with said second axis of said second housing.

8. The bone fixation assembly of claim 7, wherein said second housing comprises a locking feature configured to transition from a first state to a second state, said first state configured to allow said second housing to move relative to said interconnecting member, and said second state configured to cause said second housing to be rigidly affixed relative to said interconnecting member.

9. The bone fixation assembly of claim 7, wherein said first housing comprises a locking feature configured to transition from a first state to a second state, said first state configured to allow said first housing to be movable relative to said head segment of said bone fastener, and said second state configured to cause said first housing to be rigidly affixed relative to said head segment of said bone fastener.

10. The bone fixation assembly of claim 7, wherein said first and said second housing are configured to cooperatively interact via an extension of one of said first or second housing and a cavity of the other of said first or second housing.

11. The bone fixation assembly of claim 10, wherein said range of positions attainable by said first housing relative to said second housing is limited by said cooperative interaction between said first and said second housing.

12. The bone fixation assembly of claim 7, wherein said first housing is configured to move relative to said second housing along a trajectory that is non-parallel to said second axis of said second housing.

13. A bone fixation assembly, comprising:
an interconnecting member;
a bone fastener comprising a head segment and a shank configured to extend therefrom, said head configured to couple to a first segment of a driver configured to advance said fastener onto a bone;
a first housing comprising:
a top surface, an opposing bottom surface and at least one interconnecting side surface;
a first internal bore configured to extend from said top to said bottom surface along a first axis; and
a seat configured to accept at least a portion of said head segment of said bone fastener;
a second housing comprising:
a top surface, an opposing bottom surface and at least one interconnecting side surface;
a first bore configured to extend from a side surface to an opposing side surface of said second housing member, said first bore sized to seat said interconnecting member; and
a second bore configured to extend from said top to said bottom surface along a second axis, said second bore sized to permit advancement of said first segment of said driver therethrough; and
a locking feature configured to transition from a first state to a second state, said first state configured to enable said second housing to be movable relative to said interconnecting member, and said second state configured to cause said second housing to be rigidly immobilized relative to said interconnecting member;
wherein said second housing is configured to be movably coupled to said first housing and to slidably move relative to it along a trajectory that is non-parallel to said second axis of said first housing; and
wherein said second housing is configured to comprise a range of positions relative to said first housing, at least one of said positions comprising said first axis of said first housing being coaxially aligned with said second axis of said second housing.

14. The bone fixation assembly of claim 13, wherein said second housing comprises a locking feature configured to transition from a first state to a second state, said first state configured to enable said second housing to be movable relative to said interconnecting member, and said second state configured to cause said second housing to be rigidly immobilized relative to said interconnecting member.

15. The bone fixation assembly of claim 13, wherein said first housing comprises a locking feature configured to transition from a first state to a second state, said first state configured to enable said first housing to be movable relative to said head segment of said bone fastener, and said second state configured to cause said first housing to be rigidly immobilized relative to said head segment of said bone fastener.

16. The bone fixation assembly of claim 13, wherein said first and second housing are further configured to cooperatively interact via an extension of one of said first and second housing and a cavity of the other of said first and second housing.

17. The bone fixation assembly of claim 16, wherein said range of positions of said first housing is limited by said cooperative interaction of said first and second housing.

18. The bone fixation assembly of claim 13, wherein said first housing is configured to move relative to said second housing along a trajectory that is non-parallel to said first axis of said first housing.

19. A bone fixation assembly, comprising:
an interconnecting member;
a bone fastener comprising a head segment and a shank configured to extend therefrom, said head segment configured to couple to a first segment of a driver, said driver adapted to advance said fastener onto a bone;
a first housing comprising:
at least a top surface and an opposing bottom surface;
a first internal bore configured to extend from said top surface to said bottom surface along a first axis; and
a seat configured to receive at least a portion of said head segment of said bone fastener;
a second housing comprising:
two first surfaces configured to substantially oppose one another;
two second surfaces configured to substantially oppose one another, and configured to connect said two first surfaces to one another;
a first bore configured to extend from a first of said two second surfaces to a second of said two second surfaces, said first bore sized to receive said interconnecting member; and
a second bore configured to extend from a first of said two first surfaces to a second of said two first surfaces along a second axis, said second bore sized to permit advancement of said first segment of said driver therethrough; and a locking mechanism configured to transition from a first state to a second state, said first state configured to enable said interconnecting member to be movable relative to said head segment of said bone fastener, and said second state configured to cause said interconnecting member to be rigidly immobilized relative to said head segment of said bone fastener;
wherein said second housing is movably coupled to said first housing and configured to move relative to the first housing along a trajectory that is non-parallel to the first axis of said first housing; and
wherein said second housing is configured to assume one of a range of positions relative to said first housing when said locking mechanism is in said second state, at least one of said positions comprising said first axis of said first housing being coaxially aligned with said second axis of said second housing.

20. The bone fixation assembly of claim 19, wherein said second housing comprises a locking feature configured to transition from a first state to a second state, said first state configured to enable said second housing to be moved relative to said interconnecting member, and said second state configured to immobilize said second housing relative to said interconnecting member.

21. The bone fixation assembly of claim 19, wherein said first housing comprises a locking feature configured to transition from a first state to a second state, said first state configured to enable said first housing to move relative to said head segment of the bone fastener, and said second state configured to immobilize said first housing relative to said head segment of said bone fastener.

22. The bone fixation assembly of claim 19, wherein said movable coupling of said first and second housing comprises cooperative interaction of an extension of one of said first and second housing with a cavity of the other of said first and second housing.

23. The bone fixation assembly of claim 19, wherein said movable coupling of said first and second housing is configured to limit said range of positions.

24. The bone fixation assembly of claim 19, wherein said second housing is configured to move relative to said first housing along a trajectory that is non-parallel to said second axis of said second housing.

* * * * *